United States Patent
Divino, Jr. et al.

(10) Patent No.: US 6,676,900 B1
(45) Date of Patent: *Jan. 13, 2004

(54) METHOD FOR THE PREPARATION AND DELIVERY OF GAS-ENRICHED FLUIDS

(75) Inventors: Vincent Divino, Jr., Mission Viejo, CA (US); Seth A. Foerster, San Clemente, CA (US); James M. Gessert, Colorado Springs, CO (US); Robert A. Mest, Long Beach, CA (US); Paul J. Zalesky, Huntington Beach, CA (US); James Richard Spears, Bloomfield Hills, MI (US)

(73) Assignees: TherOx, Inc., Irvine, CA (US); Wayne State University, Detroit, MI (US)

( * ) Notice: Subject to any disclaimer, the term of this patent is extended or adjusted under 35 U.S.C. 154(b) by 447 days.

This patent is subject to a terminal disclaimer.

(21) Appl. No.: 09/699,751

(22) Filed: Oct. 30, 2000

Related U.S. Application Data

(60) Continuation of application No. 09/122,143, filed on Jul. 24, 1998, now Pat. No. 6,180,059, which is a continuation-in-part of application No. 08/915,532, filed on Aug. 15, 1997, now Pat. No. 6,607,698, which is a continuation-in-part of application No. 08/465,425, filed on Jun. 5, 1995, now Pat. No. 5,797,874, which is a division of application No. 08/353,137, filed on Dec. 9, 1994, now Pat. No. 5,599,296.

(51) Int. Cl.[7] .......................... A61M 1/36; A61M 37/00

(52) U.S. Cl. ........................ 422/45; 422/44; 604/4.01; 604/6.14; 604/6.16; 261/DIG. 28

(58) Field of Search ..................... 422/44–48; 604/4.01, 604/5.01, 6.09, 6.11–6.12, 6.14, 6.16, 264, 523–25, 529, 533–35; 261/DIG. 27, 28, 75, 76, 115; 435/1.1, 1.2, 283.1, 284.1, 286.6–286.7, 297.1, 297.2, 297.4, 818

(56) References Cited

U.S. PATENT DOCUMENTS

| | | | |
|---|---|---|---|
| 2,474,665 A | 6/1949 | Guarino | 128/214 |
| 3,142,296 A | 7/1964 | Love | 128/214 |
| 3,437,450 A | 4/1969 | Greenwood | 23/285.5 |

(List continued on next page.)

FOREIGN PATENT DOCUMENTS

| | | | |
|---|---|---|---|
| WO | WO 92/14404 | 9/1992 | A61B/6/00 |
| WO | WO 92/14976 | 9/1992 | F25B/19/00 |
| WO | WO 95/13843 | 5/1995 | A61M/37/00 |

(List continued on next page.)

OTHER PUBLICATIONS

Boe et al. "Use of hyperbaric oxygen as oxygen source in extracorporeal oxygenation of blood".*

Padmavathy Guttikonda et al., "Effect of Topical O2–Supersaturated Normal Saline on UV Light–Induced Mouse Ear Inflammation," SSID Dermatology Session Abstract, vol. 44, No. 1, p. 51A, Jan. 1996.

John Metschl, "The Supersaturation of Gases in Water and Certain Organic Liquids," vol. 28, pp. 417–437, 1924.

Frank B. Kenrick et al.,"Supersaturtion of Gases in Liquids," J. Phys. Chem., vol. 28, pp. 1308–1315, 1924.

(List continued on next page.)

*Primary Examiner*—Angela D. Sykes
*Assistant Examiner*—Patricia M Bianco
(74) *Attorney, Agent, or Firm*—Margaret A. Kivinski

(57) ABSTRACT

A gas-enriched fluid is provided by the combination of a first fluid, such as a patient's blood, with a second gas-supersaturated fluid, such as an oxygen supersaturated fluid. In this example, a catheter assembly includes a portion that receives the patient's blood from a pump and that receives the oxygen supersaturated fluid from an appropriate fluid source. The oxygen supersaturated fluid is advantageously combined with the blood in an area of laminar flow, and then this gas-enriched fluid is delivered to the patient through an appropriate lumen coupled to the portion of the catheter assembly.

12 Claims, 11 Drawing Sheets

U.S. PATENT DOCUMENTS

| | | | |
|---|---|---|---|
| 3,512,517 A | 5/1970 | Kadish et al. | 128/2 |
| 4,041,180 A | 8/1977 | Wilson | 426/11 |
| 4,317,731 A | 3/1982 | Roberts, Jr. et al. | 210/741 |
| 4,442,843 A | 4/1984 | Rasor et al. | 128/660 |
| 4,466,804 A | 8/1984 | Hino | 604/4 |
| 4,493,692 A | 1/1985 | Reed | 604/4 |
| 4,596,210 A | 6/1986 | Schmidtke | 123/1 A |
| 4,657,756 A | 4/1987 | Rasor et al. | 424/9 |
| 4,664,680 A | 5/1987 | Weber | 55/48 |
| 4,681,119 A | 7/1987 | Rasor et al. | 128/660 |
| 4,769,241 A | 9/1988 | Heldebrant et al. | 424/161 |
| 4,828,543 A | 5/1989 | Weiss et al. | 604/4 |
| 4,871,450 A | 10/1989 | Goodrich et al. | 210/151 |
| 4,874,509 A | 10/1989 | Bullock | 210/169 |
| 4,919,895 A | 4/1990 | Heldebrant et al. | 422/129 |
| 4,973,558 A | 11/1990 | Wilson et al. | 435/240.242 |
| 5,006,352 A | 4/1991 | Zelenák née Zoltai et al. | 426/67 |
| 5,084,011 A * | 1/1992 | Grady | 604/24 |
| 5,086,620 A | 2/1992 | Spears | 62/51.1 |
| 5,167,806 A | 12/1992 | Wang et al. | 210/188 |
| 5,261,875 A | 11/1993 | Spears | 604/24 |
| 5,322,500 A | 6/1994 | Johnson et al. | 604/4 |
| 5,407,426 A | 4/1995 | Spears | 4/24 |
| 5,569,180 A | 10/1996 | Spears | 604/24 |
| 5,573,505 A * | 11/1996 | Johnson et al. | 604/508 |
| 5,599,296 A | 2/1997 | Spears | 604/26 |
| 5,693,017 A | 12/1997 | Spears et al. | 604/132 |
| 5,695,717 A | 12/1997 | Polaschegg et al. | 422/48 |
| 5,709,654 A | 1/1998 | Klatz et al. | 604/24 |
| 5,725,492 A | 3/1998 | Igo et al. | 604/4 |
| 5,730,330 A | 3/1998 | Reading | 222/113 |
| 5,730,698 A | 3/1998 | Fischell et al. | 600/3 |
| 5,730,935 A | 3/1998 | Spears | 422/44 |
| 5,735,934 A | 4/1998 | Spears | 75/414 |
| 5,752,929 A | 5/1998 | Klatz et al. | 604/51 |
| 5,766,490 A | 6/1998 | Taylor et al. | 210/758 |
| 5,797,874 A | 8/1998 | Spears | 604/53 |
| 5,797,876 A | 8/1998 | Spears et al. | 604/95 |
| 5,814,222 A | 9/1998 | Zelenák et al. | 210/615 |
| 5,834,519 A | 11/1998 | Spears | 514/938 |
| 5,843,307 A | 12/1998 | Faivre et al. | 210/192 |
| 5,849,191 A | 12/1998 | Agranonik et al. | 210/608 |
| 5,874,093 A | 2/1999 | Eliaz et al. | 424/401 |
| 5,879,282 A | 3/1999 | Fischell et al. | 600/3 |
| 5,885,467 A | 3/1999 | Zelenák et al. | 210/758 |
| 5,893,838 A | 4/1999 | Daoud et al. | 604/26 |
| 5,922,305 A | 7/1999 | Spears | 424/43 |
| 5,957,880 A | 9/1999 | Igo et al. | 604/4 |
| 5,957,899 A | 9/1999 | Spears et al. | 604/264 |
| 5,958,377 A | 9/1999 | Spears | 424/43 |
| 6,007,774 A | 12/1999 | Faithfull et al. | 422/44 |
| 6,180,059 B1 * | 1/2001 | Divino et al. | 422/45 |

FOREIGN PATENT DOCUMENTS

| | | | |
|---|---|---|---|
| WO | WO 96/10593 | 1/1996 | A61B/19/00 |
| WO | WO 96/17565 | 6/1996 | A61F/5/00 |
| WO | WO 96/40334 | 12/1996 | A61M/15/00 |
| WO | WO 96/41987 | 12/1996 | |
| WO | WO 97/19713 | 6/1997 | |
| WO | WO 97/49447 | 12/1997 | A61M/25/00 |
| WO | WO 98/16203 | 4/1998 | A61K/9/133 |

OTHER PUBLICATIONS

Robert B. Dean, "The Formation of Bubbles," Journal of Applied Physics, vol. 15, pp. 446–451, May 1944.

C. Boe et al., "Use of Hyperbaric Oxygen as Oxygen Source in Extracorporeal Oxygenation of Blood," Physiological and Clinical Aspects of Oxygenator Design, Elsevier North–Holland Biomedical Press, Luxembourg, 1976.

Pieter Stroev et al., "Supersaturated fluorocarbon as an oxygen source," Physiological and Clinical Aspects of Oxygenator Design, Elsevier North–Holland Biomedical Press, pp. 129–139, Luxembourg, 1976.

Edvard A. Hemmingsen, "Cavitation in gas–supersaturated solutions," Journal of Applied Physics, vol. 46, No. 1, pp. 213–218, Jan. 1976.

Wayne A. Gerth et al., "Gas Supersaturation Thresholds for Spontaneous Cavitation in Water with Gas Equilibration Pressure up to 570 atml," Z. Naturforsch, 31a, pp. 1711–1716, Oct. 5, 1976.

Edvard A. Hemmingsen, "Effects of Surfactants and Electrolytes on the Nucleation of Bubbles in Gas–Supersaturated Solutions," Z. Naturforsch, 33a, pp. 164–171, Oct. 25, 1977.

Yehuda Finkelstein et al., "Formation of Gas Bubbles in Supersaturated Solutions of Gases in Water," AIChE Journal, vol. 13, No. 9, pp. 1409–1419, Sep., 1985.

Mordecai B. Rubin et al., "Measurements of Critical Supersaturation for Homogeneous Nucleation of Bubbles," American Chemical Society, Dec. 9, 1986.

"Fluosol® % Intravascular Perfluorochemical Emulsion Product Information," Alpha Therapeutic Corporation, Los Angeles, California, pp. 1–8, Dec. 1989.

J. Richard Spears et al., "Potential Intravascular Oxygenation with Oxygen Clathrate Hydrate," (Abstract 388), Abstracts from the 65$^{th}$ Scientific Sessions, Circulation, vol. 80, Suppl. I, p. 1–97, 1992.

Brian A. Cason et al., "Effects of High Arterial Oxygen Tension on Function, Blood Flow Distribution, and Metabolism in Ischemic Myocardium," Circulation, vol. 85, No. 2, pp. 828–838, Feb. 1992.

Taijiro Sueda et al., "Evaluation of Two New Liquid–Liquid Oxygenators," ASAIO Journal, pp. 923–928, 1993.

Brian A. Cason, et al., "Therapeutic Hyperoxia Diminishes Myocardial Stunning," J Card Surg, pp. 459–464, 1994.

J. Richard Spears et al., "Myocardial Protection with a Perfusion Guidewire During Balloon Angioplasty in a Canine Model," (Abstracts/Poster 1032–30), JACC, vol. 27, Suppl. A, p. 392A, Feb. 1996.

J. Richard Spears, "Advances in the Management of Respiratory Failure—Aqueous Preparations of Oxygen," American Society for Artificial Internal Organs, Inc., vol. 42, No. 3, May–Jun., 1996.

J. Richard Spears et al., "Hyperoxemic Perfusion with Aqueous Oxygen Improves LV Function During Experimental M1–Reperfusion," (Abstract 2038), Circulation, vol. 96, Abstracts from the 70$^{th}$ Scientific Sessions, Supplement I, pp. I–364–I–365, 1997.

Richard Maas et al., "Superoxygenation Process Treats Highly Concentrated Wastewaters," WATER/Engineering & Management, pp. 29–33, 39, Feb. 1997.

J. R. Spears et al., "Intraaortic Infusion of Oxygen in a Rabbit Model," (Abstracts/Poster 1014–155), JACC, vol. 29, Suppl. A, pp. 317A–318A, Feb. 1997.

Adrian H. Shandling et al., "Hyperbaric oxygen and thrombolysis in myocardial infarction: The "HOT MI" Pilot Study," American Heart Journal, vol. 134, No. 3, pp. 544–550, Sep. 1997.

J. Richard Spears et al. Aqueous Oxygen: A Highly $O_2$-Supersaturated Infusate for Hyperoxemic Treatment of Postischemic Myocardium, (Abstract/Poster TCT–262), The American Journal of Cardiology, Sep. 1997.

J. Richard Spears et al., "Aqueous Oxygen—A Highly $O_2$-Supersaturated Infusate for Regional Correction of Hypoxemia and Production of Hyperoxemia," Circulation, vol. 96, No. 12, pp. 4385–4391, Dec. 16, 1997.

G.J. Brereton et al., "Nucleation in small capillary tubes," Chemical Physics 230, pp. 253–265, 1998.

J.R. Spears et al., "Hyperoxemic Reperfusion With Aqueous Oxygen Improves Left Ventricular Function and Microvascular Flow in the Postischemic Canine Myocardium," (Abstract 1185–127), JACC, vol. 31 (Suppl. A) p. 449A, Feb. 1998.

Product Monograph, Fluosol® 20% Intravascular Perfluorochemical Emulsion, "Delivers Oxygen to Protect the Heart During PTCA," Alpha Therapeutic Corporation, pp. 3–30.

E. Newton Harvey et al., "Bubble Formation In Animals," J. Cell. Comp. Physiol., vol. 24, pp. 23–34.

* cited by examiner

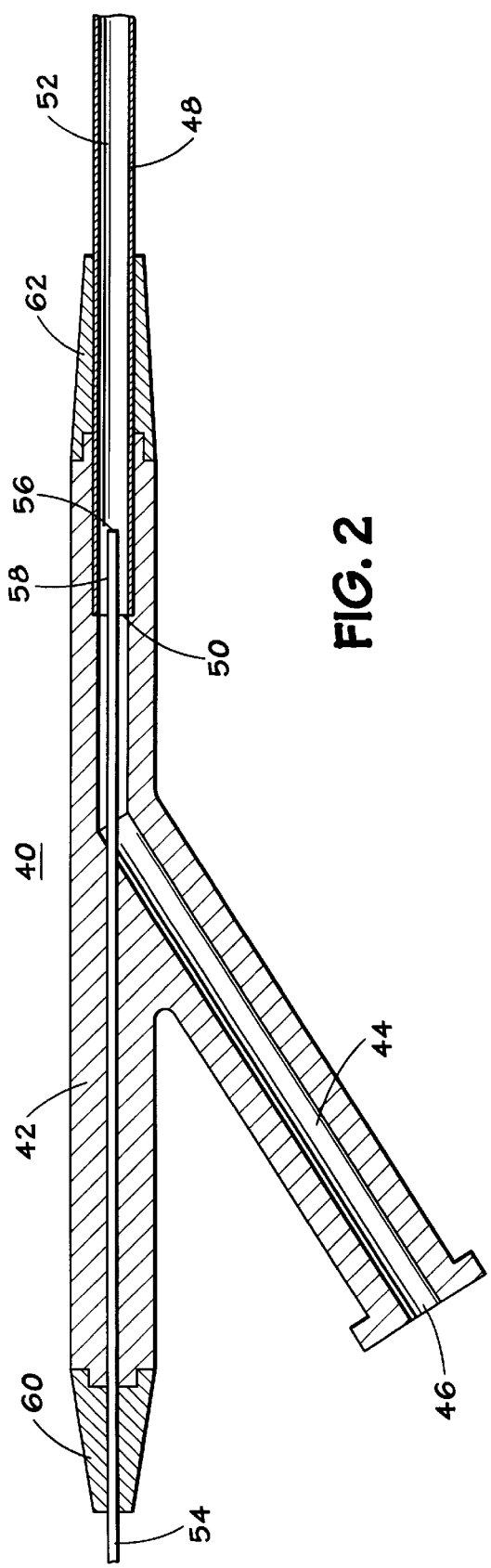
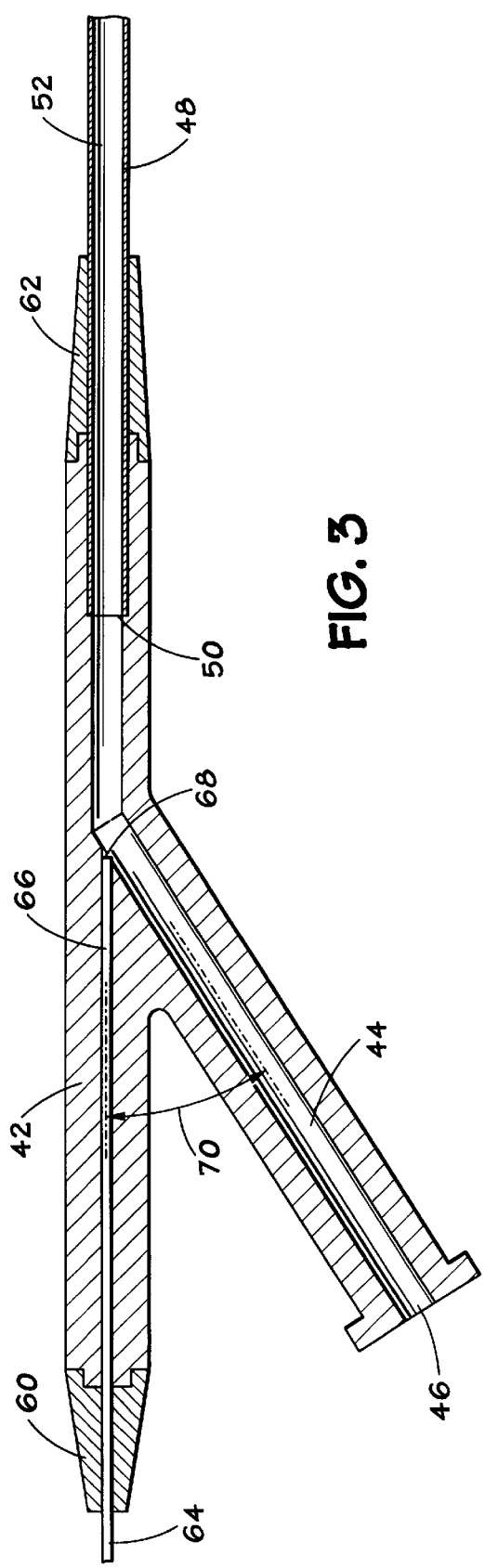

FIG. 5
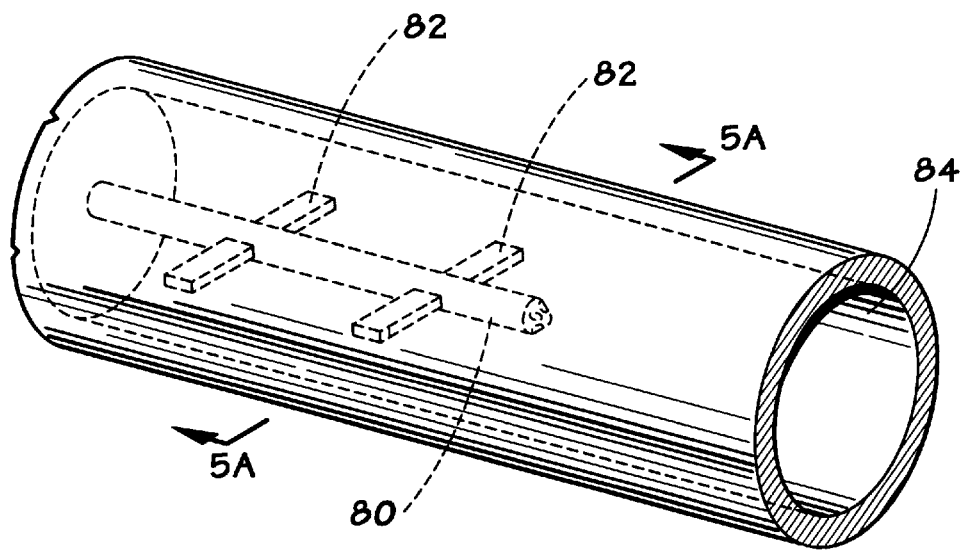
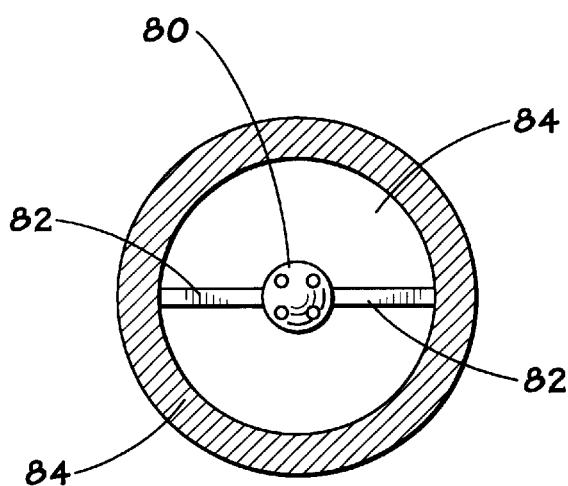
FIG. 5A
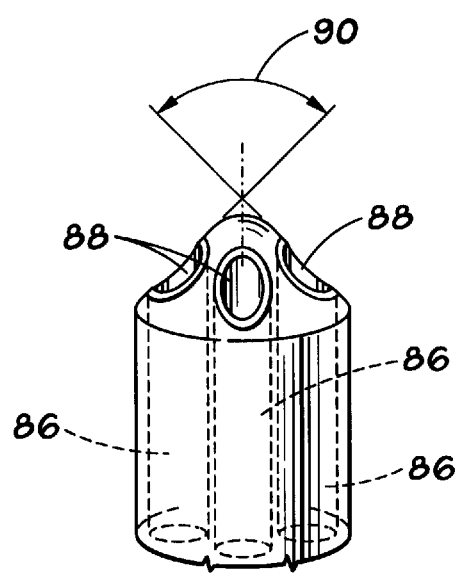
FIG. 5B

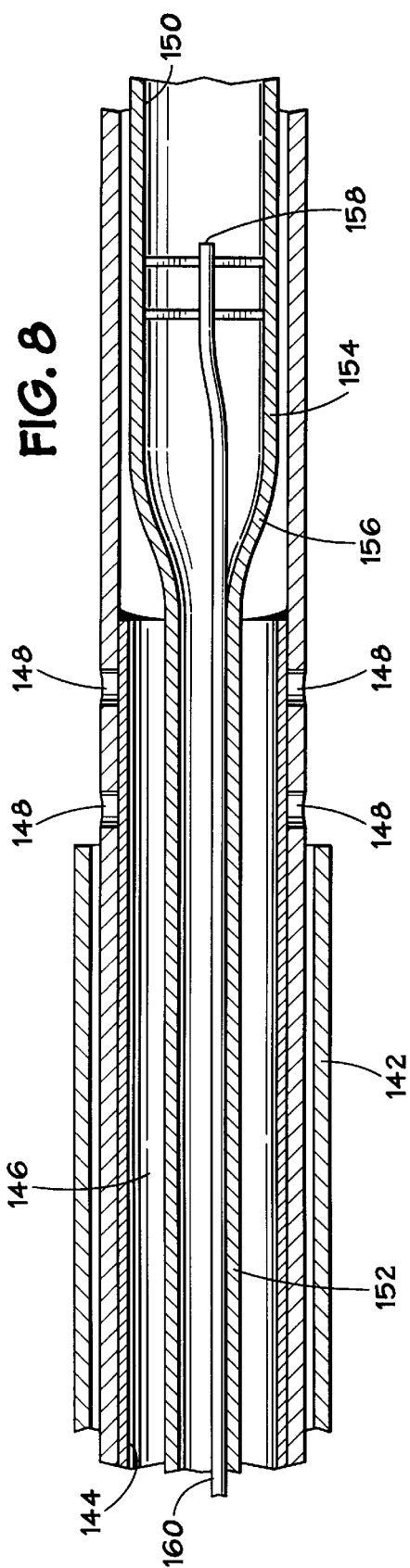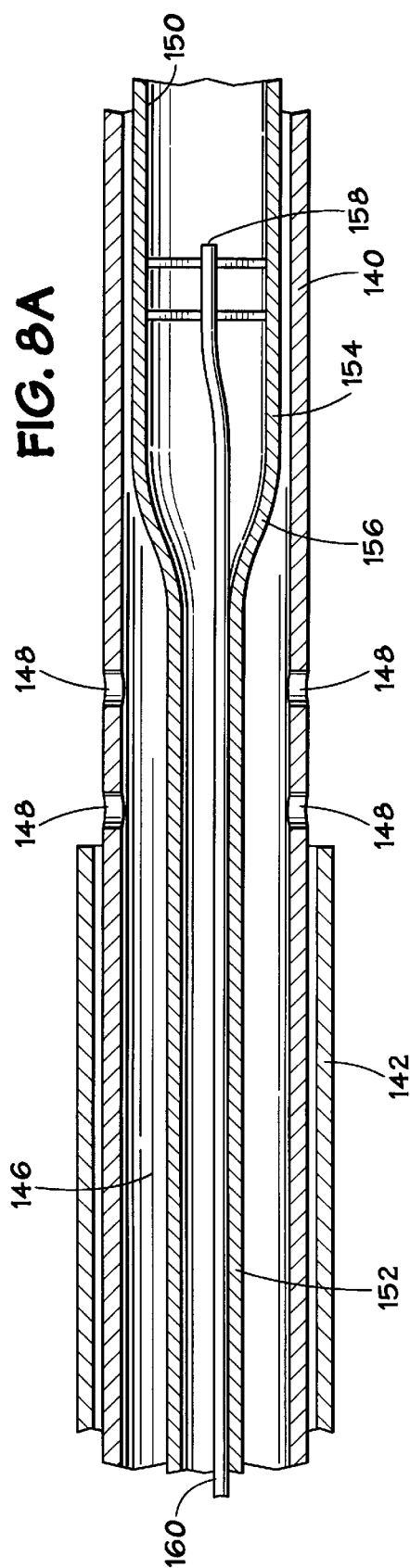

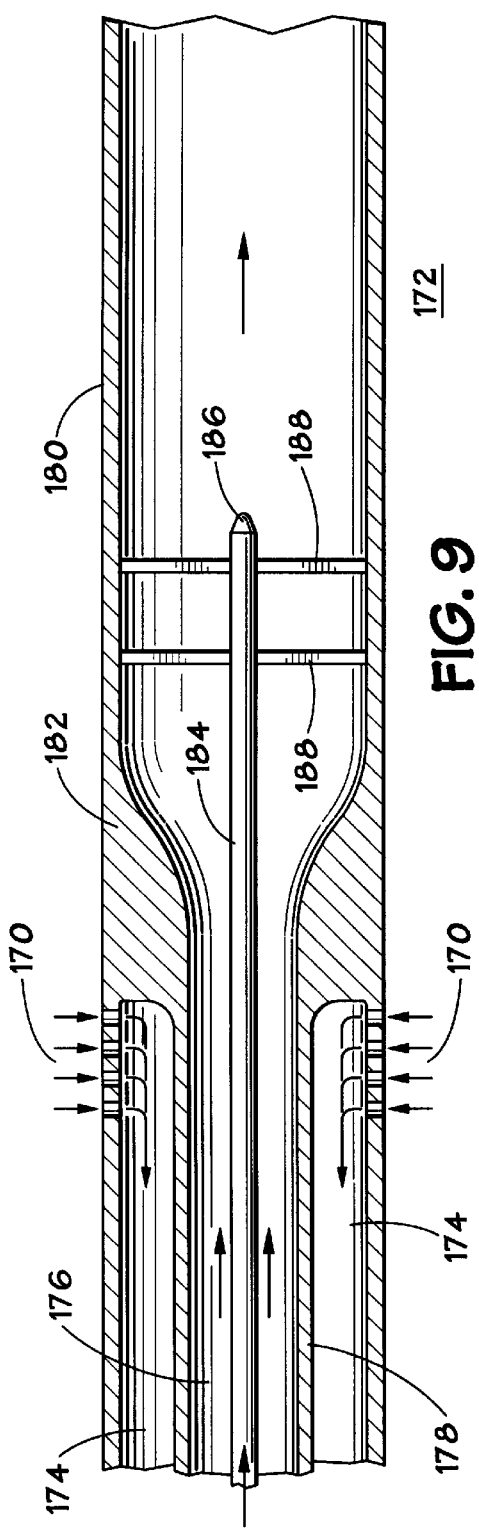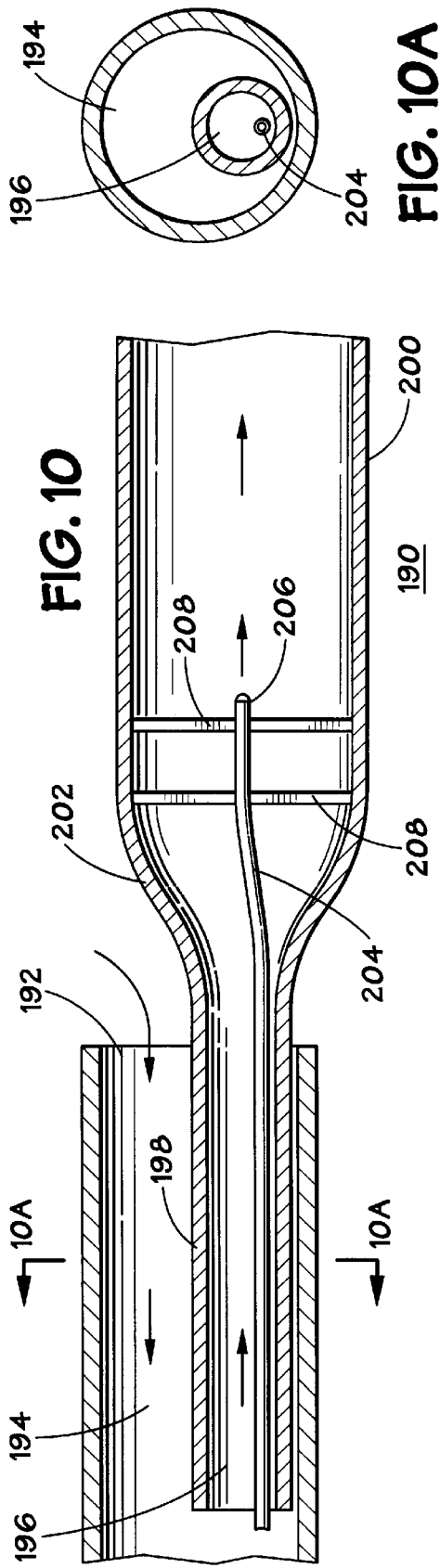

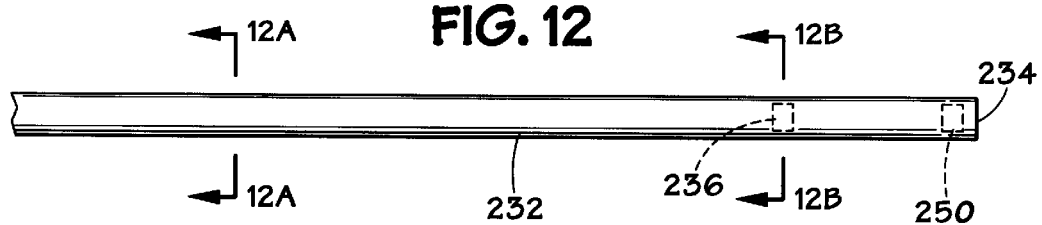
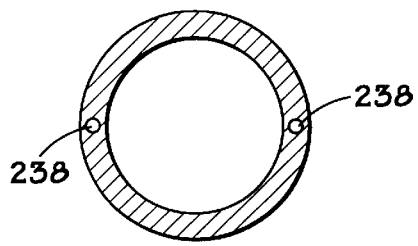
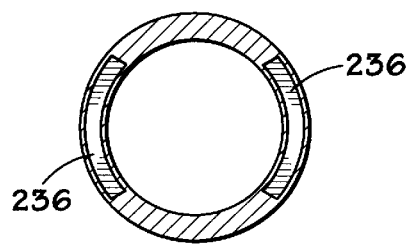
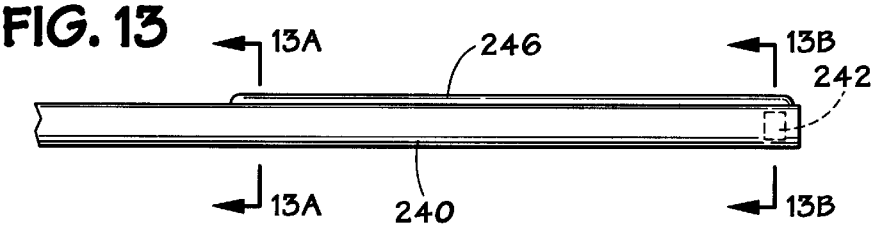
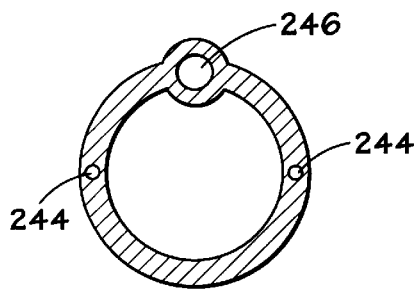
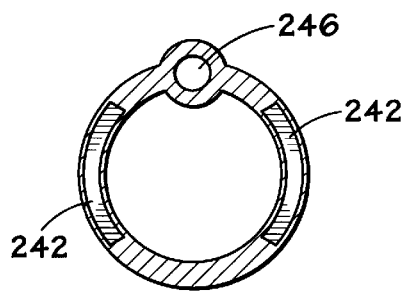
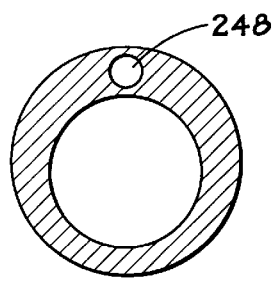
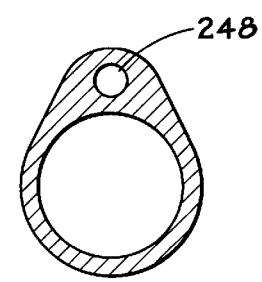

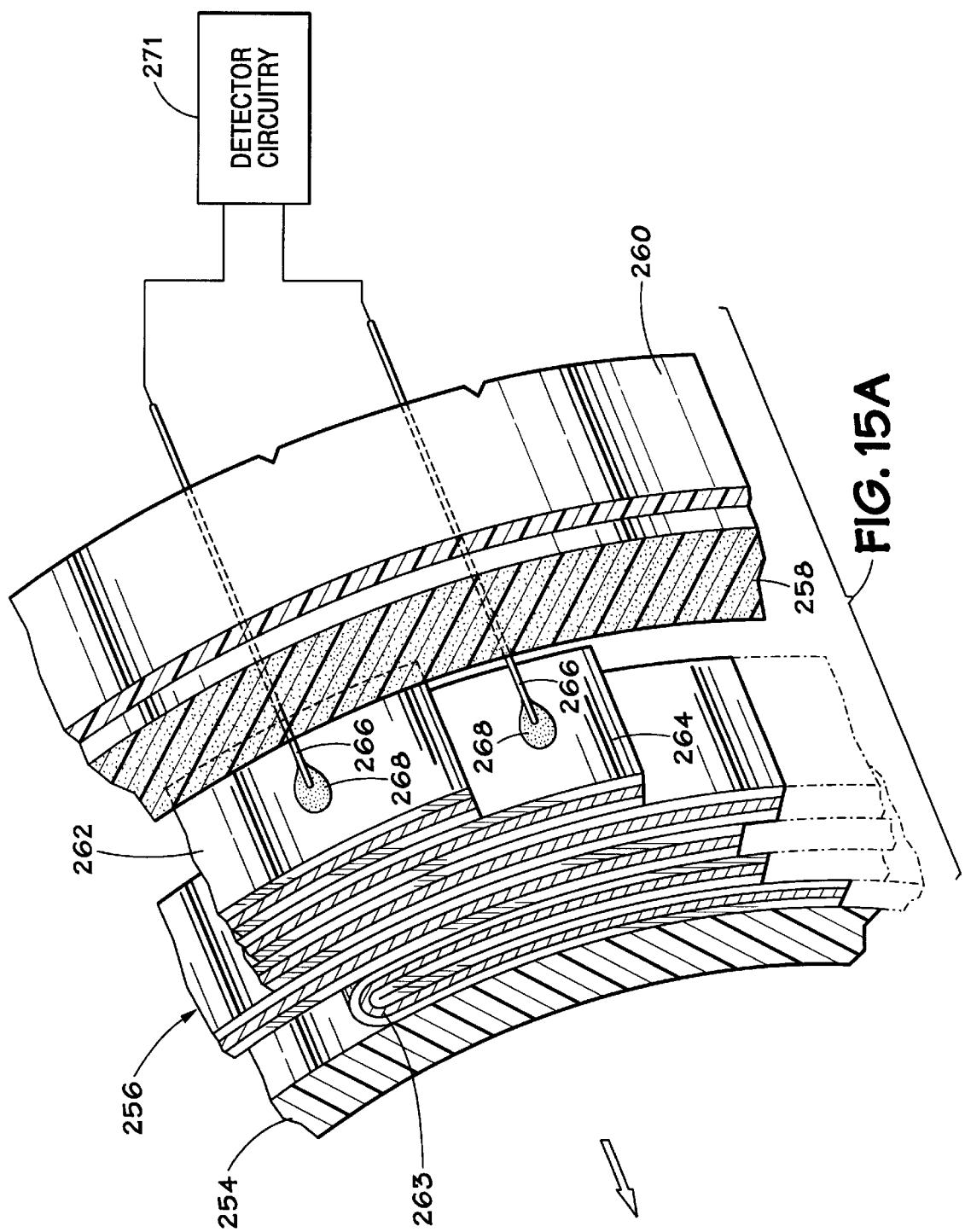

METHOD FOR THE PREPARATION AND DELIVERY OF GAS-ENRICHED FLUIDS

RELATED APPLICATIONS

This application is a continuation of U.S. patent application Ser. No. 09/122,143, filed on Jul. 24, 1998, entitled "Method for the Preparation and Delivery of Gas-Enriched Fluids," which issued on Jan. 30, 2001, as U.S. Pat. No. 6,180,059, which is a continuation-in-part of U.S. patent application Ser. No. 08/915,532, filed on Aug. 15, 1997, now U.S. Pat. No. 6,607,698, entitled "Method for Generalized Extracorporeal Support," by Spears et al., and which is also a continuation-in-part of U.S. patent application Ser. No. 08/465,425, filed on Jun. 5, 1995, entitled "Method of Delivery of Gas-Supersaturated Liquids," by Spears, which issued on Aug. 25, 1998, as U.S. Pat. No. 5,797,874, which is a divisional of U.S. patent application Ser. No. 08/353,137, filed on Dec. 9, 1994, entitled "Apparatus and Method of Delivery of Gas-Supersaturated Liquids," by Spears, which issued on Feb. 4, 1997, as U.S. Pat. No. 5,599,296, all of which are incorporated herein by reference.

FIELD OF THE INVENTION

The present invention relates generally to an apparatus and method for the preparation and delivery of gas-enriched fluids to gas-depleted locations, and more particularly, to a system and method for the preparation and delivery of physiologic solutions for treating conditions such as tissue ischemia and post-ischemic tissues, including, inter alias a catheter for delivering oxygen-enriched blood to specific locations within a patient's body.

BACKGROUND OF THE INVENTION

Oxygen is a crucial nutrient for human cells. Cell damage may result from oxygen deprivation for even brief periods of time, which may lead to organ dysfunction or failure. For example, heart attack and stroke victims experience blood flow obstructions or diversions that prevent oxygen from being delivered to the cells of vital tissues. Without oxygen, the heart and brain progressively deteriorate. In severe cases death results from complete organ failure. Less severe cases typically involve costly hospitalization, specialized treatments and lengthy rehabilitation.

Blood oxygen levels may be described in terms of the partial pressure of the oxygen dissolved in the blood ($pO_2$). Typically, for arterial blood, normal blood oxygen levels (i.e., normoxia or normoxemia) range from 90–110 mm Hg. Hypoxemic blood (i.e., hypoxemia) is arterial blood with a $pO_2$ less than 90 mm Hg. Hyperoxic blood (i.e., hyperoxemia or hyperoxia) is arterial blood with a $pO_2$ greater than 400 mm Hg (see Cason et. al (1992), Effects of High Arterial Oxygen Tension on Function, Blood Flow Distribution, and Metabolism in Ischemic Myocardium, *Circulation*, Vol. 85, No. 2, pp. 828–838), but less than 760 mm Hg (see Shandling et al. (1997), Hyperbaric Oxygen and Thrombolysis in Myocardial Infarction: The "HOT MI" Pilot Study, *American Heart Journal*, Vol. 134, No. 3, pp. 544–550). Hyperbaric blood is arterial blood with a $pO_2$ greater than 760 mm Hg. Venous blood typically has a $pO_2$ level less than 90 mm Hg. In the average adult, for example, normal venous blood oxygen levels range generally from 40 mm Hg to 70 mm Hg.

Blood oxygen levels also might be described in terms of hemoglobin saturation levels. For normal arterial blood, hemoglobin saturation is about 97% and varies only slightly as $pO_2$ levels increase. For normal venous blood, hemoglobin saturation is about 75%.

In patients who suffer from acute myocardial infarction, if the myocardium is deprived of adequate levels of oxygenated blood for a prolonged period of time, irreversible damage to the heart can result. Where the infarction is manifested in a heart attack, the coronary arteries fail to provide adequate blood flow to the heart muscle.

Treatment of acute myocardial infarction or myocardial ischemia often comprises performing angioplasty or stenting of the vessels to compress, ablate or otherwise treat the occlusion(s) within the vessel walls. For example, a successful angioplasty increases the size of the vessel opening to allow increased blood flow.

Even with the successful treatment of occluded vessels, a risk of tissue injury may still exist. During percutaneous transluminal coronary angioplasty (PTCA), the balloon inflation time is limited by the patient's tolerance to ischemia caused by the temporary blockage of blood flow through a vessel during balloon inflation. Reperfusion injury also may result, for example, due to slow coronary reflow or no reflow following angioplasty.

For some patients angioplasty procedures are not an attractive option for the treatment of vessel blockages. Such patients typically are at increased risk of ischemia for reasons such as, poor left ventricular function, lesion type and location, or the amount of the myocardium at risk. The treatment options for such patients thus include more invasive procedures such as coronary bypass surgery.

To reduce the risk of tissue injury typically associated with treatments of acute myocardial infarction and myocardial ischemia, it is usually desirable to deliver oxygenated blood or oxygen-enriched fluids to at-risk tissues. Tissue injury is minimized or prevented by the diffusion of the dissolved oxygen from the blood or fluids to the tissue and/or blood perfusion that removes metabolites and that provides other chemical nutrients.

In some cases, the desired treatment of acute myocardial infarction and Myocardial ischemia includes perfusion of oxygenated blood or oxygen-enriched fluids. During PTCA, for example, tolerated balloon inflation time may be increased by the concurrent introduction of oxygenated blood into the patient's coronary artery. Increased blood oxygen levels also may cause the normally perfused left ventricular cardiac tissue into hypercontractility to further increase blood flow through the treated coronary vessels.

The infusion of oxygenated blood or oxygen-enriched fluids also may be continued following the completion of PTCA treatment or other procedures (e.g. surgery) wherein cardiac tissue "stunning" with associated function compromise has occurred. In some cases continued infusion may accelerate the reversal of ischemia and facilitate recovery of myocardial function.

Conventional methods for the delivery of oxygenated blood or oxygen-enriched fluids to at-risk tissues involve the use of blood oxygenators. Such procedures generally involve withdrawing blood from a patient, circulating it through an oxygenator to increase blood oxygen concentration, and then delivering the blood back to the patient. One example of a commercially available blood oxygenator is the Maxima blood oxygenator manufactured by Medtronic, Inc., Minneapolis, Minn.

There are drawbacks, however, to the use of a conventional oxygenator in an extracorporeal circuit for oxygenating blood. Such systems typically are costly, complex and difficult to operate. Often a qualified perfusionist is required to prepare and monitor the system.

Conventional oxygenator systems also typically have a large priming volume, i.e., the total volume of bloodcontained within the oxygenator, tubing and other system components, and associated devices. It is not uncommon in a typical adult patient case for the oxygenation system to hold more than one to two liters of blood. Such large priming volumes are undesirable for many reasons. For example, in some cases a blood transfusion may be necessary to compensate for the blood temporarily lost to the oxygenation system because of its large priming volume. Heaters often must be used to maintain the temperature of the blood at an acceptable level as it travels through the extracorporeal circuit. Further, conventional oxygenator systems are relatively difficult to turn on and off. For instance, if the oxygenator is turned off, large stagnant pools of blood in the oxygenator might coagulate.

In addition, with extracorporeal circuits including conventional blood oxygenators there is a relatively high risk of inflammatory cell reaction and blood coagulation due to the relatively slow blood flow rates and the large blood contact surface area. A blood contact surface area of about 1–2 $m^2$ and velocity flows of about 3 cm/s are not uncommon with conventional oxygenator systems. Thus, relatively aggressive anti-coagulation therapy, such as heparinization, is usually required as an adjunct to using the oxygenator.

Perhaps one of the greatest disadvantages to using conventional blood oxygenation systems is that the maximum partial pressure of oxygen ($pO_2$) that can be imparted to blood with commercially available oxygenators is about 500 mm Hg. Thus, blood $pO_2$ levels near or above 760 mm Hg cannot be achieved with conventional oxygenators.

Some experimental studies to treat myocardial infarction have involved the use of hyperbaric oxygen therapy. See, e.g., Shandling et al. (1997), Hyperbaric Oxygen and Thrombolysis in Myocardial Infarction: The "HOT MI" Pilot Study, *American Heart Journal*, Vol. 134, No. 3, pp. 544–550. These studies generally have involved placing patients in chambers of pure oxygen pressurized at up to 2 atmospheres, resulting in systemic oxygenation of patient blood up to a $pO_2$ level of about 1200 mm Hg. However, use of hyperbaric oxygen therapy following restoration of coronary artery patency in the setting of an acute myocardial infarction is not practical. Monitoring critically ill patients in a hyperbaric oxygen chamber is difficult. Many patients become claustrophobic. Ear damage may occur. Further, treatment times longer than 90 minutes cannot be provided without concern for pulmonary oxygen toxicity.

For these reasons, the treatment of regional organ ischemia generally has not been developed clinically. Thus, there remains a need for a simple and convenient system for delivering oxygen-enriched blood and other fluids to patients for the localized prevention of ischemia and the treatment of post-ischemic tissue and organs.

SUMMARY OF THE INVENTION

The present invention may address one or more of the problems set forth above. Certain possible aspects of the present invention are set forth below as examples. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present invention, a system for the preparation and delivery of a gas-enriched fluid is provided. In applications involving the prevention of ischemia or the treatment of ischemic tissues, the system may be used for the preparation and delivery of an oxygen-enriched fluid including blood to a specific location within a patient's body. The system may include a circuit for oxygenating or enriching blood, e.g., increasing the level of dissolved oxygen in the blood. The system includes an apparatus that combines a gas-supersaturated fluid with blood to form a gas-enriched fluid, advantageously for regional or localized delivery. The gas-supersaturated fluid may include an oxygen-supersaturated physiologic liquid, and the blood to be enriched is blood withdrawn from the patient.

The system provided further includes assemblies for supplying controlled flows or supplies of the gas-supersaturated fluid and the blood. The system includes an elongated, generally tubular assembly including a central lumen and at least one end placeable within a patient body proximate a tissue site to be treated, the end including an outlet port for the gas-enriched fluid. The system may include a catheter defining a fluid pathway, including a proximal portion adapted for coupling to supplies of gas-supersaturated fluid and blood, and a distal portion defining a fluid pathway removably insertable within a patient's body, for infusing the gas-enriched fluid to predetermined sites.

In an alternate embodiment of the present invention, the proximal portion of the catheter is adapted for coupling to a supply of gas-supersaturated fluid, and includes a pump loop through which blood drawn from a blood inlet flows. The blood inlet comprises a porous side segment or axial sleeve defining the entry into an annular conduit that transitions into a lumen in fluid communication with the pump loop. The inlet is disposed along the portion of the catheter removably insertable within the patient's body. Upon insertion of the catheter through an access or opening, e.g., an introducer sheath, and upon its placement within the patient body, e.g., tip placement in or proximate the coronary ostium, the blood inlet is distal to the access sheath so as to permit blood from the patient to pass through and along the fluid path defined by the blood inlet, annular conduit, lumen and pump loop before combining with the gas-supersaturated fluid to form the gas-enriched fluid delivered to the patient via the catheter central lumen and outlet port.

In another embodiment of the present invention, a method is provided for the preparation and delivery of a gas-enriched fluid. In applications involving the prevention of ischemia or the treatment of ischemic tissues, the method may include the step of combining a gas-supersaturated fluid with blood to form a gas-enriched fluid. Advantageously, the gas-supersaturated fluid comprises an oxygen-supersaturated physiologic liquid in which oxygen is dissolved at concentrations normalized to standard temperature and pressure (STP) that equal or exceed the volume of the solvent. Examples of solvents which may be used include saline, lactated Ringer's, and other water-based physiologic solutions.

In accordance with another embodiment of the present invention, a method is provided for delivering an oxygen-enriched fluid to a specific site within a patient's body. The method comprises raising the $pO_2$ level of the fluid to be supplied to the patient. Where the fluid to be infused includes blood, the method may include the step of controlling or providing controlled amounts of the blood and oxygen-supersaturated fluid that are combined so as to produce an oxygen-enriched fluid for delivery to a specific predetermined site. Blood $pO_2$ levels may be maintained, adjusted, or otherwise controlled by controlling the flow rates or by providing controlled amounts of the blood and/or oxygen-supersaturated fluid. Thus, a blood-gas control method is provided.

Furthermore, delivery of the gas-enriched fluid advantageously occurs without the formation of clinically significant bubbles. To help minimize or eliminate the formation of clinically significant bubbles, the blood contact surfaces are exposed to or coated with blood proteins for some brief time interval, usually at least several minutes, before the start of infusion of oxygen-supersaturated fluid. Also, fluid contact surfaces are exposed to or pre-wetted with liquids, e.g., saline, ethanol and benzalkonium heparin, before use. The fluid contact surfaces also do not include any substance which promotes such bubble formation, e.g., hydrophobic surfaces that are difficult to wet, teflon, teflon-composite liners, silicone oils, etc. Hydrophillic fluid contact surfaces are typically useful.

The embodiments may be used in conjunction with angiographic or guiding catheters, arterial sheaths, and/or other devices used in angioplasty and in other interventional cardiovascular procedures. The system may be used in applications involving one or more vascular openings, i.e., in either contralateral or ipsilateral procedures.

In contralateral procedures blood is withdrawn from the patient at a first location, e.g., the left femoral artery. The blood is enriched and then is returned to the patient at a second location proximate the tissue to be treated. Blood enrichment occurs as the blood pumped through the extracorporeal circuit or loop is combined with the gas-supersaturated fluid to form the gas-enriched fluid to be delivered. In applications where the system includes a catheter, the catheter may include proximal and distal ends and a central lumen. The proximal end is adapted for the catheter to receive a supply of the gas-supersaturated fluid and to receive the blood. The distal end is removably insertable within a patient's body through a second location such as the patient's right femoral artery. The distal end includes at least one port in fluid communication with the central lumen and through which the gas-enriched fluid may exit. Further, the distal portion of the catheter may be adapted with a tip portion shaped so as to promote insertion of the device, such as through the same sheath used for interventional procedures like angioplasty, to specific pre-determined locations within a patient's body. Examples of tip portion shapes which may be used include any of the standard clinically accepted tip configurations used with devices like guide catheters for providing access to and for holding in locations like the coronary ostium. Accordingly, the method may further include the step of positioning the portion of the distal end of the catheter including the fluid exit port at a predetermined location within a patient body proximate to the tissue to be treated.

In ipsilateral procedures, the system may be used along with one or more of any of a number of suitable, standard-size, clinically accepted guide catheters and/or introducer sheaths. The system, for example, may comprise a catheter, a catheter and guide catheter, or a catheter and sheath, for use within a guide catheter or introducer sheath used for the primary interventional procedure. In accordance with this embodiment of the present invention, blood is drawn between the catheter and guide catheter or sheath assemblies of the present invention, between the catheter assembly of the present invention and the guide catheter or introducer sheath used for the primary interventional procedure, or from the annular space between the guide catheter and the introducer sheath.

As described herein, the preferred gas-supersaturated fluid for use in accordance with the present invention is an oxygen-supersaturated fluid. However, other fluids may be used depending upon the circumstances involved in a particular desired application, such as, for example, supersaturated fluids in which one or more gases such as helium, nitrous oxide, carbon dioxide and air are dissolved. The oxygen-supersaturated fluid may include a dissolved oxygen volume normalized to standard temperature and pressure of between about 0.5 and about 3 times the volume of the solvent. The fluid is supplied to the system at a pressure of between about 250 p.s.i. and about 5000 p.s.i. The exact pressure may vary depending upon the circumstances involved in a particular application. Further, the oxygen-supersaturated fluid supplied may be a sterile fluid which does not include gas, surface, or bubble nucleation sites at which clinically significant bubbles may form.

Exemplary apparatus and methods for preparing oxygen-supersaturated fluids are disclosed in U.S. Pat. No. 5,407,426 to Spears entitled "Method and Apparatus for Delivering Oxygen into Blood"; U.S. Pat. No. 5,569,180 to Spears entitled "Method for Delivering a Gas-Supersaturated Fluid to a Gas-Depleted Site and Use Thereof"; and U.S. Pat. No. 5,599,296 to Spears entitled "Apparatus and Method of Delivery of Gas-Supersaturated Liquids"; each of which is incorporated herein by reference. Furthermore, disclosure relating to exemplary apparatus and methods for the preparation and/or use of gas-supersaturated fluids, including, e.g., oxygen-supersaturated fluids, in various applications, may be found in the following patents and patent applications, each of which is incorporated herein by reference:

copending U.S. patent application Ser. No. 08/465,425, filed Jun. 5, 1995, now U.S. Pat. No. 5,797,874 which is a division of U.S. patent application Ser. No. 353,137, filed Dec. 9, 1994, now U.S. Pat. No. 5,599,296, which is a continuation in part of U.S. patent application Ser. No. 273,652, filed Jul. 12, 1994, now U.S. Pat. No. 5,569,180, which is a continuation in part of U.S. patent application Ser. No. 152,589, filed Nov. 15, 1993, now U.S. Pat. No. 5,407,426, which is a continuation in part of U.S. patent application Ser. No. 818,045, filed Jan. 8, 1992, now U.S. Pat. No. 5,261,875, which is a continuation of U.S. patent application Ser. No. 655,078, filed Feb. 14, 1991, now U.S. Pat. No. 5,086,620;

copending U.S. patent application Ser. No. 08/581,019, filed Jan. 3, 1996, which is a continuation in part of U.S. patent application Ser. No. 273,652, filed Jul. 12, 1994, now U.S. Pat. No. 5,569,180, which is a continuation in part of U.S. Pat. application Ser. No. 152,589, filed Nov. 15, 1993, now U.S. Pat. No. 5,407,426, which is a continuation in part of U.S patent application Ser. No. 818,045, filed Jan. 8, 1992, now U.S. Pat. No. 5,261,875, which is a continuation of U.S. patent application Ser. No. 655,078, filed Feb. 14, 1991, now U.S. Pat. No. 5,086,620; and copending U.S. patent application Ser. No. 08/840,908, filed Apr. 16, 1997, which is a continuation in part of U.S. patent application 453,660, filed May 30, 1995, now U.S. Pat. No. 5,735,934, which is a division of U.S. patent application Ser. No. 273,652, filed Jul. 12, 1994, now U.S. Pat. No. 5,569,180, which is a continuation in part of U.S. patent application Ser. No. 152,589, filed Nov. 15, 1993, now U.S. Pat. No 5,407,426, which is a continuation in part of U.S. patent application Ser. No. 818,045, filed Jan. 8, 1992, now U.S. Pat. No. 5,261,875, which is a continuation of U.S. patent application Ser. No. 655,078, filed Feb. 14, 1991, now U.S. Pat. No. 5,086,620.

The catheter system of the present invention is typically sized in accordance with the circumstances involved in a particular application. In general, the sizes of the various system components will be on the order of the sizes of clinically accepted interventional cardiovascular devices. Usually, the extracorporeal loop of the present invention is less than four meters in total length. Thus, for example, where the system supports blood flow rates between 100 ml/min and 175 ml/min, the priming volume would be approximately 35 ml.

BRIEF DESCRIPTION OF THE DRAWINGS

Further objects and advantages of the present invention will become apparent upon reading the following detailed description and upon referring to the accompanying drawings in which:

FIG. 2 is a cross-sectional view of part of an exemplary embodiment of a catheter system including an angled blood flow path in accordance with the present invention.

FIG. 3 is a cross-sectional view of part of an alternate exemplary embodiment of a catheter system including an angled blood flow path in accordance with the present invention.

FIG. 5 is a perspective view of part of an exemplary embodiment of a catheter system including an exemplary oxygen-supersaturated fluid outlet in accordance with the present invention.

FIG. 5A is a cross-sectional view along line A—A in FIG. 5 of the part of the exemplary embodiment of a catheter system including an exemplary oxygen-supersaturated fluid outlet shown in accordance with the present invention.

FIG. 5B is a view of the exemplary oxygen-supersaturated fluid outlet shown in FIG. 5 in accordance with the present invention.

FIG. 8 is a cross-sectional view of part of an exemplary guide catheter including a liner used with an exemplary embodiment of a catheter system in accordance with the present invention.

FIG. 8A is a cross-sectional view of the exemplary guide catheter shown in FIG. 8, without the liner, in accordance with the present invention.

FIG. 9 is a cross-sectional view of part of an exemplary catheter system including an integral blood draw comprising a porous side blood inlet in accordance with the present invention.

FIG. 10 is a cross-sectional view of part of an exemplary catheter system including an integral blood draw comprising an axial blood inlet in accordance with the present invention.

FIG. 10A is a cross-sectional view along line A—A in FIG. 10 of the part of an exemplary catheter system shown in accordance with the present invention.

FIG. 12 is a cross-sectional view of an exemplary tip configuration of a catheter in accordance with the present invention.

FIG. 12A is a cross-sectional view along line A—A in FIG. 12 of an exemplary tip configuration of a catheter in accordance with the present invention.

FIG. 12B is a cross-sectional view along line B—B in FIG. 12 of an exemplary tip configuration of a catheter in accordance with the present invention.

FIG. 13 is a cross-sectional view of an alternate exemplary tip configuration of a catheter in accordance with the present invention.

FIG. 13A is a cross-sectional view along line A—A in FIG. 13 of an alternate exemplary tip configuration of a catheter in accordance with the present invention.

FIG. 13B is a cross-sectional view along line B—B in FIG. 13 of an alternate exemplary tip configuration of a catheter in accordance with the present invention.

FIG. 14 is a cross-sectional view of an alternate exemplary tip configuration of a catheter in accordance with the present invention.

FIG. 14A is a cross-sectional view of a further alternate exemplary tip configuration of a catheter in accordance with the present invention.

FIG. 15A is a partially exploded view of a portion of the bubble detector transducer shown in FIG. 15.

Figure 1:
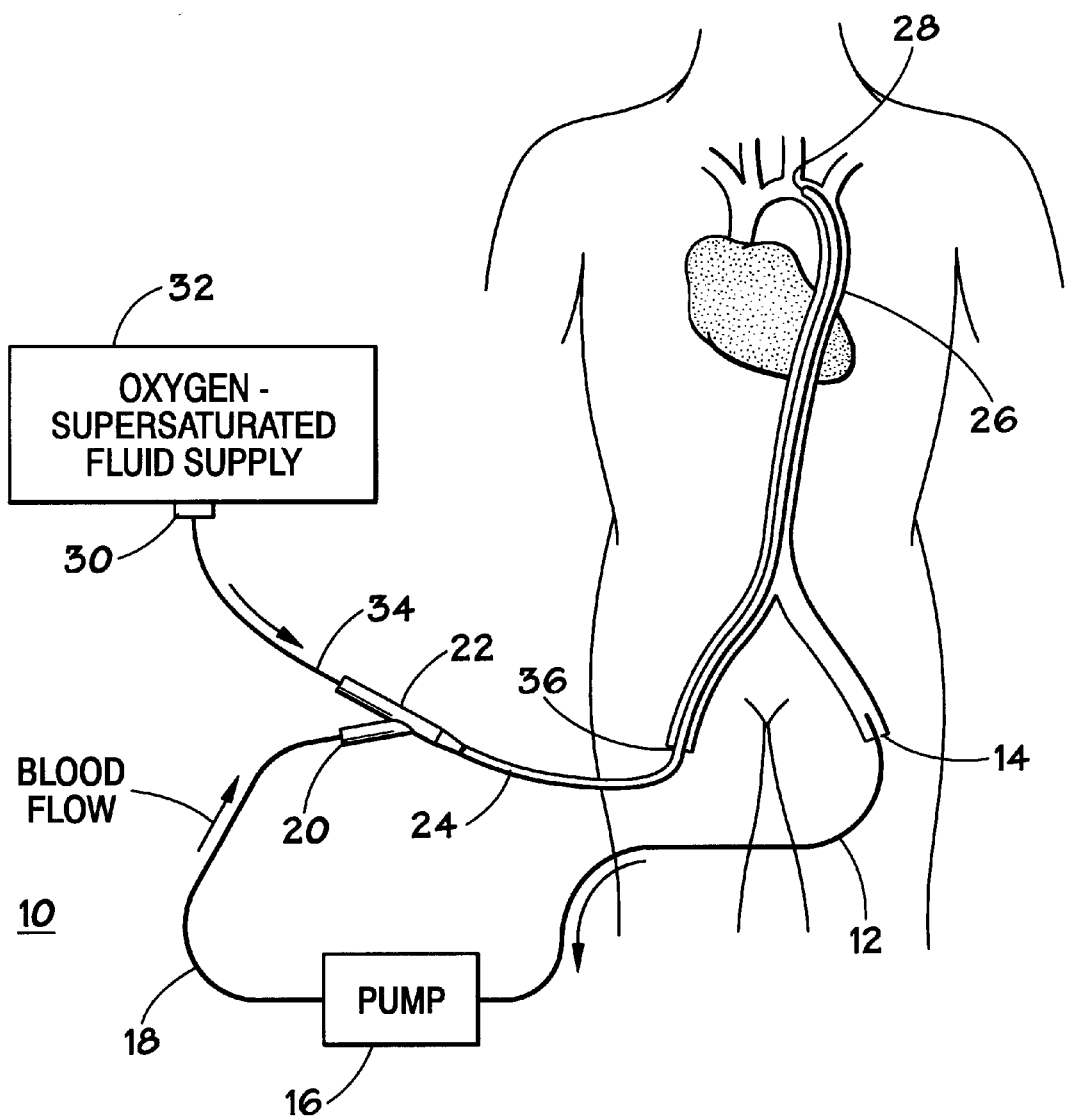
FIG. 1 is a schematic diagram of an exemplary embodiment of a catheter system used in a contralateral interventional procedure in accordance with the present invention.

The present invention may be susceptible to various modifications and alternative forms. Specific embodiments of the present invention are shown by way of example in the drawings and are described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

DETAILED DESCRIPTION OF SPECIFIC EMBODIMENTS

The description below illustrates embodiments of the present invention. For the sake of clarity, not all features of an actual implementation of the present invention are described in this specification. It should be appreciated that in connection with developing any actual embodiment of the present invention many application-specific decisions must be made to achieve specific goals, which may vary from one application to another. Further, it should be appreciated that any such development effort might be complex and time-consuming, but would still be routine for those of ordinary skill in the art having the benefit of this disclosure.

For the sake of clarity and convenience, the various embodiments are described herein in the context of interventional cardiovascular applications generally involving acute or transient ischemia or post-ischemic tissues. However, the present invention may also useful in other medical applications, such as cancer therapy (e.g., the delivery of oxygen-enriched fluids directly into poorly vascularized tumors during radiation or chemotherapy treatments), neurovascular applications (e.g., the treatment of stroke and cerebral trauma patients), lung support in trauma and lung disease patients, and wound care management.

Also, although the present invention may be used to raise oxygen levels, for example, in venous and arterial blood, in blood substitutes, e.g., perfluorocarbons, and in combinations thereof, for the sake of clarity arid convenience reference is made herein only to arterial blood.

Further, the present invention also may be used in connection with drug fluid infusion therapies. Examples of drug fluids used in cardiovascular and neurological procedures which may be infused in accordance with the present invention include, without limitation, vasodilators (e.g., nitroglycerin and nitroprusside), platelet-actives (e.g., ReoPro and Orbofiban), thrombolytics (e.g., t-PA, streptokinase, and urokinase), antiarrhythmics (e.g., lidocaine, procainamide), beta blockers (e.g., esmolol, inderal), calcium channel blockers (e.g., diltiazem, verapamil), magnesium, inotropic agents (e.g., epinephrine, dopamine), perofluorocarbons (e.g., fluosol), crystalloids (e.g., normal saline, lactated ringers), colloids (albumin, hespan), blood products (packed red blood cells, platelets, whole blood), Na+/H+ exchange inhibitors, free radical scavengers, diuretics (e.g., mannitol), antiseizure drugs (e.g., phenobarbital, valium), and neuroprotectants (e.g., lubeluzole).

Turning now to the drawings, a system is provided in which blood is combined with an oxygen-supersaturated fluid to form an oxygen-enriched fluid that may be delivered to a particular predetermined area within a patient's body for the treatment of conditions such as tissue ischemia and post-ischemic tissues. As shown in FIG. 1, one embodiment of such a system 10 includes a blood draw 12 comprising a continuous fluid flow path between a vascular access site 14 of a patient body and a pump 16. The selection of the vascular access site typically is made by a physician or caregiver and depends upon the circumstances surrounding the particular application involved. The particular vascular access site illustrated in FIG. 1 is the left femoral artery. The blood pump 16 may be one of the many commercially available and clinically accepted blood pumps suitable for use with human patients. An example of one such pump is the Model 6501 RFL3.5 Pemco peristaltic pump available from Pemco Medical, Cleveland, Ohio.

The pump 16 draws blood, from the patient and provides a supply of blood via line 18 to the inlet 20; of catheter 22; The flow characteristics of the blood will depend upon the circumstances surrounding the particular application involved. Typically, the supply of blood to the blood inlet 20 of catheter 22 will be a controlled flow defined by the flow parameters selected by the caregiver. Factors influencing the determination of blood flow characteristics may include one or more of the many clinical parameters or variables of the blood to be supplied to the catheter or of the oxygen-enriched fluid to be delivered to the patient, e.g., the size of the patient, the percentage of overall circulation to be provided, hemolysis, hemodilution, $pO_2$, pulsatility, mass flow rate, volume flow rate, temperature, hemoglobin concentration and pH.

The system 10 may include one or more gas bubble detectors, at least one of which is capable of detecting the presence of microbubbles, i.e., bubbles with diameters of about 7 to 10 microns to about 200 microns (see, e.g., FIG. 12). In addition, the system may include one or more macrobubble detectors to detect larger bubbles, such as bubbles with diameters of 1 millimeter or more. Such macrobubble detectors may comprise any suitable commercially available detector, such as an outside, tube-mounted bubble detector including two transducers measuring attenuation of a sound pulse traveling from one side of the tube to the other. One such suitable detector may be purchased from Transonic Inc. of New York. The microbubble and macrobubble detectors provide the physician or caregiver with a warning of potentially clinically significant bubble generation. The system 10 also may include various conventional items such as sensors, flow meters (which may also serve a dual role as a macrobubble detector), or other clinical parameter monitoring devices; hydraulic components such as accumulators and valves for managing flow dynamics; access ports which permit withdrawal of fluids; filters or other safety devices to help ensure sterility; or other devices that generally may assist in controlling the flow of one or more of the fluids in the system 10. Advantageously, any such devices are positioned within the system and used so as to avoid causing the formation of clinically significant bubbles within the fluid flow paths.

The catheter 22 includes a proximal portion 24 and a distal portion 26, the distal portion being removably insertable within a patient body through a vascular access or opening 36. The proximal portion 24 includes blood inlet 20. Blood inlet 20 and line 18 may be adapted for releasably coupling, e.g., with a clinically accepted fluid connection apparatus such as a Luer lock, to enable the catheter 22 to receive the blood supplied via line 18. The catheter 22 includes a lumen defining a continuous blood flow path from the blood inlet 20 to a fluid exit port proximate the distal tip 28 of catheter 22.

The proximal portion 24 of catheter 22 also includes a fluid inlet port 30 adapted to couple to a supply 32 of oxygen-supersaturated fluid. The port 30 is in fluid communication with the supply 32 and with line 34. Line 34 comprises one or more capillaries or other elongated generally tubular members including central lumens, either alone or in an array, each defining a continuous fluid flow path between port 30 and the blood flow path of the catheter 22.

The oxygen-supersaturated fluid is usually supplied to port 30 in accordance with parameters specified and selected by the caregiver for the desired clinical indication. The flow of oxygen-supersaturated fluid is generally steady and continuous, although variable or intermittent flows may be used. Flow rates may range from about 0.1 cc/min to about 46 cc/mm, although particularly advantageous flow rates may be between about 2 cc/min and 12 cc/min. Oxygen concentrations may range from about 0.5 cc $O_2$ per cc physiologic solution to about 3 cc $O_2$ per cc physiologic solution, although particularly advantageous concentrations may be about 1 cc $O_2$ per cc physiologic solution. The oxygen-supersaturated fluid is provided at a temperature such that when the fluid combines with blood to form the oxygen-enriched fluid to be infused, the oxygen-enriched fluid is about 37° C., i.e., system operation does not significantly affect patient blood temperature.

FIG. 2 shows an embodiment in which catheter portion 40 comprises a section of the catheter in which the flows of blood and oxygen-supersaturated fluid combine. Catheter portion 40 comprises the proximal end of an elongated tubular member 48, including a generally centrally disposed fluid return lumen 52, disposed within a housing 42 including a blood inlet lumen 44. Lumen 44 defines a continuous fluid flow path between catheter blood inlet port 46 and the proximal end 50 of fluid return lumen 52. The distal portion of member 48 (not shown) is removably insertable within a patient body and includes the exit port through which fluid traveling within fluid return lumen 52 is delivered to a site within a patient's body.

Housing 42 typically comprises a biocompatable, molded polymeric material. The exact size and shape of housing 42 may vary depending upon the circumstances involved in a particular application; FIG. 2, by way of example, shows a generally y-shaped configuration. The tubular member 48 may be integrally formed with, housing 42. However, tubular member 48 may comprise clinically approved polymeric tubing. The proximal end of member 48 is fixedly attached within housing 42. Typically, the joining of housing 42 and member 48 is accomplished by solvent or adhesive bonding or insert or over molding.

The size and shape of lumen 44 also may vary depending upon the circumstances involved in a particular application. FIG. 2, by way of example, shows a lumen 44 defining an angled blood flow path. However, a straight or curved blood flow path might also be used. See, e.g., FIG. 4. Advantageously, any difference between the inner diameter of the proximal end of member 48 and the diameter of lumen 44 at the proximal end 50 of fluid return lumen 52 is minimized or eliminated to promote smooth blood flow.

Catheter portion 40 also includes the distal portion of an oxygen-supersaturated fluid delivery line 54. The line 54 comprises at least one elongated generally tubular member including a central lumen defining a fluid flow path between a fluid inlet port (not shown in FIG. 2) disposed at the proximal end of line 54 and fluid exit port 56 disposed at the distal end 58 of line 54. Catheter portion 40 also may include one or more stress/strain relief assemblies 60, 62.

The proximal end of line 54 may be adapted to releasably couple to a supply of oxygen-supersaturated fluid. The fluid exit port 56 may be disposed within the flow path defined by fluid return lumen 52. Thus, a continuous fluid flow path is defined between the supply of oxygen-supersaturated fluid and a predetermined site within a patient's body proximate the distal end of fluid return lumen 52;

The portions proximate to fluid exit port 56 of fluid return lumen 52 and of the distal end 58 of line 54 are generally straight, and their longitudinal axes approximately coincide, so that any difference in the direction of blood flow in lumen 52 proximate port 56 and the direction of exit fluid flow through port 56 is minimized or eliminated.

As shown in FIG. 2, fluid exit port 56 may be sufficiently downstream of the proximal end 50 of fluid return lumen 52 that the fluid exiting port 56 avoids any fluid flow disruption or non-laminar flow associated with the boundary between housing 42 and member 48 that might cause the formation of clinically significant gas bubbles. However, where any such flow disruptions or non-laminar flows are minimized or eliminated, the exit port for the oxygen-supersaturated fluid may be disposed upstream of the proximal end of the fluid return lumen. See, e.g., FIGS. 3 and 4. Further, as shown in FIG. 3, in an alternate embodiment, an oxygen-supersaturated fluid line 64 may include a distal portion 66 including a fluid exit port 68 at the outer boundary of lumen 44. For example, as shown in FIG. 3, the longitudinal axis of line 64 proximate port 68 and the longitudinal axis of the portion of lumen 44 downstream of port 68 advantageously coincide, while the longitudinal axis of line 64 proximate port 68 and the longitudinal axis of the portion of lumen 44 upstream of port 68 advantageously form an angle 70 comprising an acute angle which permits the smooth introduction of fluid from line 64 into the blood flow through lumen 44. Advantageously, the angle 70 may be about thirty degrees, for instance.

Figure 4:
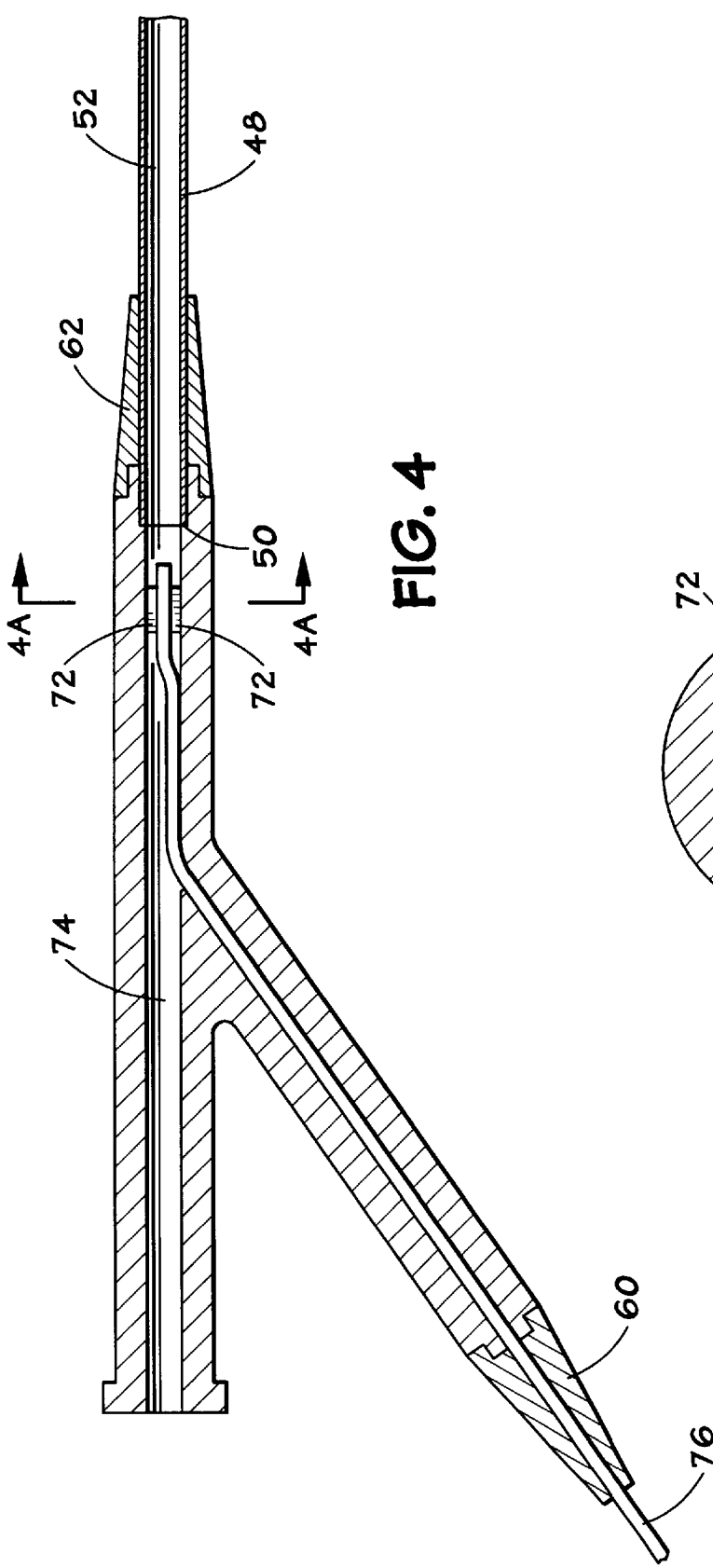
FIG. 4 is a cross-sectional view of part of another exemplary embodiment of a catheter system including a straight blood flow path in accordance with the present invention.
Figure 4A:
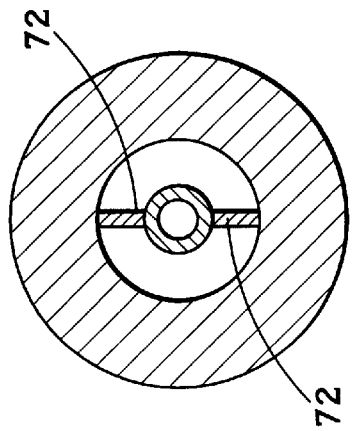
FIG. 4A is a cross-sectional view along line A—A in FIG. 4 of the exemplary embodiment of a catheter system including a straight blood flow path shown in accordance with the present invention.

As shown in FIG. 2, the portion of line 54 extending from housing 42 into the blood flow path may be rigid enough to comprise a cantilever-like member. However, as shown in FIG. 4, the extending portion of the oxygen-supersaturated fluid flow line 76 also may comprise a more flexible member which tends to align itself naturally within blood flow lumen 74 along the path of least resistance. The distal end of line 76 may be supported in place or otherwise oriented within the lumen 74 by one or more wings 72 extending between the distal end of oxygen-supersaturated line 76 and the outer wall or boundary defining lumen 74. The flexibility and positioning of the lines 54 and 76 depend upon the circumstances involved in a particular application, e.g., the material hardness, line profile, the number of capillaries making up the line, and the desired fluid exit location.

The oxygen-supersaturated fluid is injected so as to minimize or avoid altogether blood cell damage. An exemplary oxygen-supersaturated fluid outlet is shown in FIG. 5. The oxygen supersaturated fluid line 80 is disposed within fluid delivery lumen 84. The distal tip of line 80 is oriented within lumen 84 by one or more ribs or spacers 82 securing the distal portion of line 80. The line 80 includes one or more capillaries 86 (see FIG. 5B) each including a central lumen 88 through which oxygen-supersaturated fluid flows. The configuration of the distal tip of line 80 advantageously minimizes or eliminates flow disruptions resulting from the exit of fluid from each lumen 88 into the flow of blood within lumen 84. By way of example, FIG. 5B shows a line 80 comprising four capillaries 86 and including a distal tip of generally conical shape. The ends of each capillary 86 may form an included angle 90 of about 52 degrees, for instance. The capillaries may be made of glass sheathed in polyimide, with ground and polished distal ends to help minimize or eliminate the formation of clinically significant bubbles and fluid flow disruptions. The line 80 may include four 100 micron inner diameter by 350 micron outer diameter tubes, for instance, potted together with epoxy at their proximal and distal ends.

However, the inner diameter may be in the range of about 20 to about 1000 microns, with an inner diameter of about 100 to about 125 microns being particularly advantageous. Of course the exact size and shape of the distal end and tip of line 80 may vary depending upon the circumstances involved in a particular application. Examples of possible configurations include, without limitation, flat, blunt, squared, pencil-shaped, curved, parabolic, hyperbolic, and pyramidal.

Figure 6:
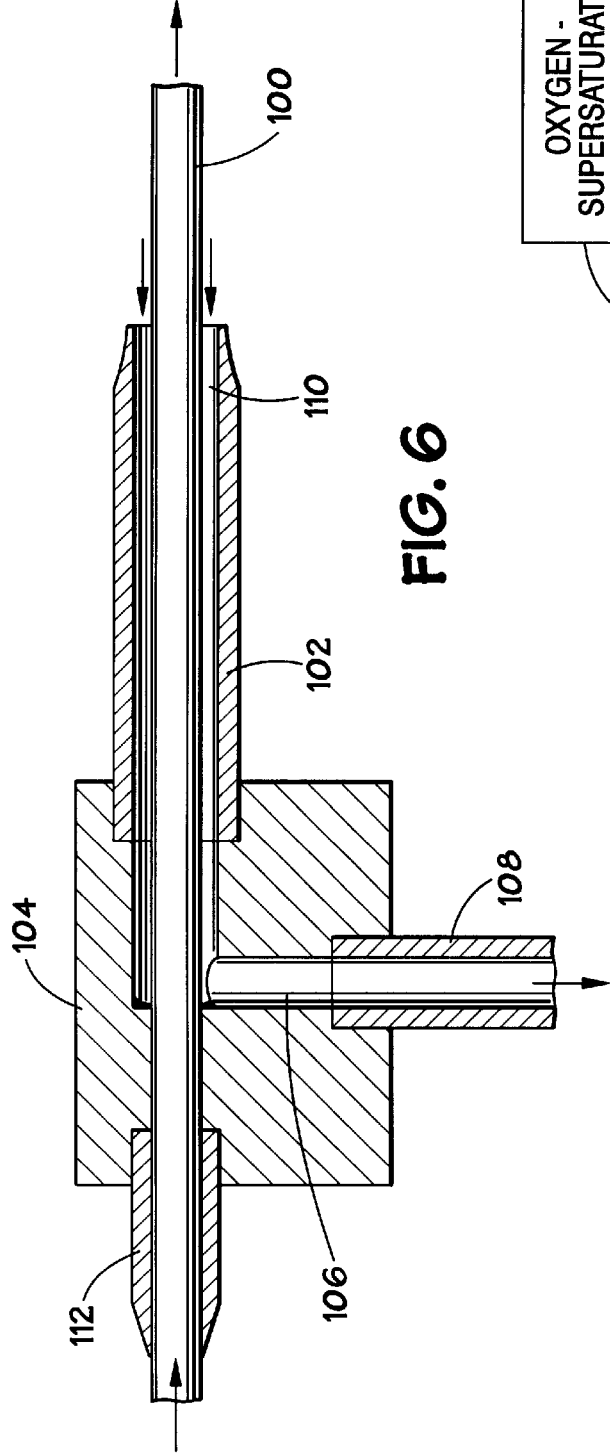
FIG. 6 is a cross-sectional view of part of an exemplary embodiment of a catheter system including an integrated blood inlet introducer sheath in accordance with the present invention.

In the embodiment shown in FIG. 6, the catheter includes an oxygen-enriched fluid return line 100 and a blood draw assembly comprising a sheath 102 and housing 104. The housing 104 includes a lumen 106 which forms a blood flow path between the lumens of sheath 102 and tube 108. Tube 108 comprises the line which supplies blood to the bloodpump (not shown in FIG. 6) of the system. The line 100 is generally centrally disposed through the housing 104 and within the central lumen of the sheath 102. Upon insertion of the distal portion of line 100 into a patient's body, the sheath 102 is positioned within a vascular access sheath, guide catheter, or other such access device, so that blood from the patient may enter the annular space 110 between the outer wall of line 100 and the inner wall of sheath 102. The proximal end of line 100 may include a stress/strain relief assembly 112.

Figure 7:
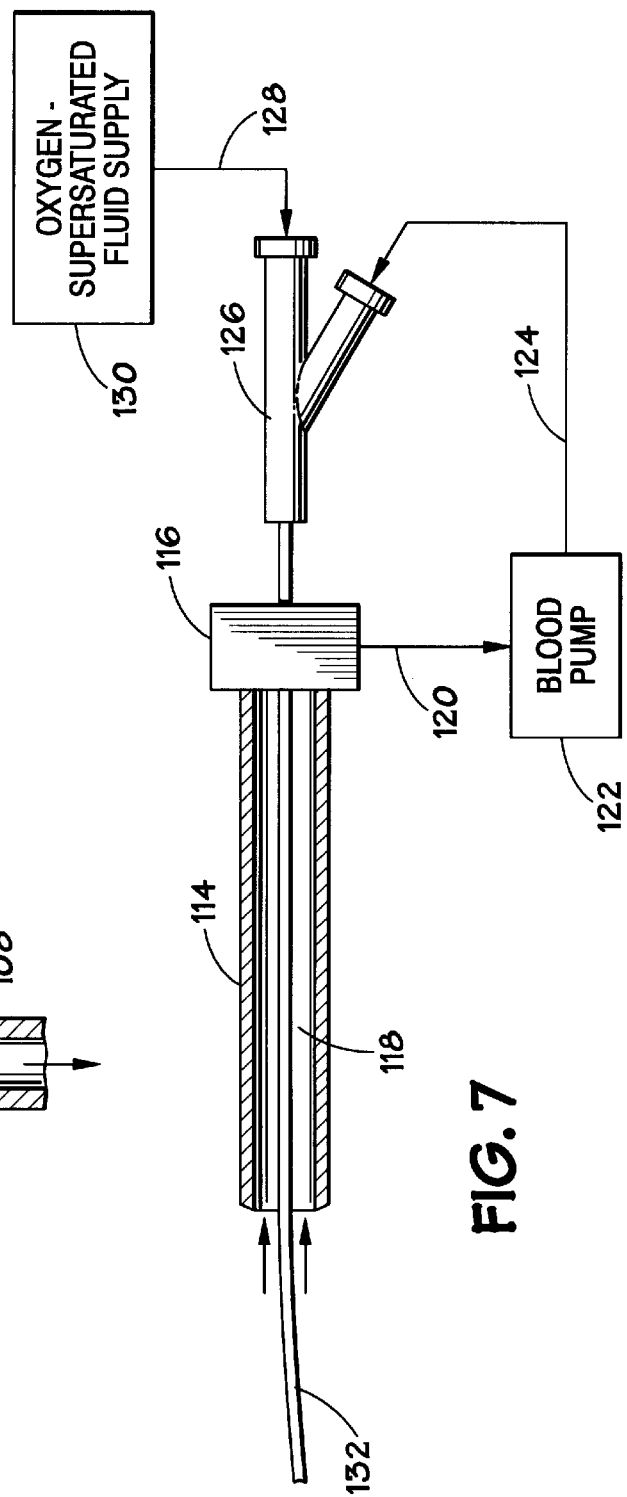
FIG. 7 is a schematic diagram of an exemplary embodiment of a catheter system for use in an ipsilateral interventional procedure in accordance with the present invention.

FIG. 7 is a schematic diagram illustrating a use of the catheter system with a separate arterial access sheath 114. The sheath 114 may be one of the many sizes and types of clinically accepted arterial access sheaths suitable for use in interventional cardiovascular procedures. The proximal end 116 of sheath 114 is adapted with a seal or other such device which permits the insertion of catheters, guidewires, or other interventional devices through the sheath 114 and into the body without unnecessary loss of blood. Blood drawn through the lumen 118 of sheath 114 travels via line 120 to blood pump 122 before being enriched and returned to the body. The blood returns via line 124 and the catheter portion 126, where the blood flow combines with a flow of oxygen-supersaturated fluid delivered via line 128 from a supply 130 to form the oxygen-enriched fluid delivered to the patient via the distal portion 132 of the catheter system.

FIGS. 8 and 8A show an alternate embodiment of the catheter system. In accordance with this embodiment, a guide catheter 140 including a distal tip (not shown) removably insertable within a patient's body is placed through an outer arterial access sheath 142. The sheath 142 may be any one of the many types of clinically accepted sheaths typically used in interventional cardiovascular procedures to gain access to a patient's vasculature. The guide catheter 140 includes a liner 144. The liner 144 is deformable and may be either partially (not shown) or completely (see FIG. 8A) removed. When a positive pressure is applied to lumen 146 of guide catheter 140, e.g., when angiographic dyes are introduced into the lumen 146, and when the liner 144 is in place covering the blood inlet holes 148 through the wall of guide catheter 140, the liner 144 presses against and closes inlet holes 148. When a negative pressure is applied to lumen 146 of guide catheter 140, e.g., during the withdrawal of blood from the patient, the liner deforms as necessary to allow the entry of blood into lumen 146 through inlet holes 148.

To facilitate the draw of blood from the patient, the fluid return line 150 may include a proximal portion 152 having smaller internal and external diameters than the distal portion 154 of line 150. When the distal tip of line 150 (not shown) is in place within the patient's body proximate a predetermined site, the transition region 156 is disposed downstream of blood inlet holes 148 so as to permit the entry of blood into lumen 146. The transition region 156 comprises a section of the line 150 in which the external and internal diameters of the line 150 increase along its length. To minimize or eliminate the formation of clinically significant bubbles, downstream of transition region 156 the flow of blood in line 150 combines with oxygen-supersaturated fluid exiting at the end 158 of oxygen-supersaturated fluid supply tube 160. As described herein (see, e.g., FIG. 5), the tube 160 may comprise either a single capillary or tube, or a bundle of capillaries or tubes.

FIG. 9 describes part of a catheter system including an integral blood draw comprising an annular porous side blood inlet 170. The catheter 172 may be used along with a guide catheter or access sheath (not shown in FIG. 9). Blood is drawn from the patient and through the inlet 170 into catheter outer lumen 174. From there, the blood circulates through a blood pump and is delivered back to the patient via catheter inner lumen 176. As shown in FIG. 9, the inner lumen 176 includes a proximal portion 178 having relatively smaller internal and external diameters than distal portion 180, and a transition region 182 joining the two portions. Oxygen-supersaturated fluid supply tube 184 includes a fluid exit port 186 disposed within the distal portion 180 of catheter 172. The fluid exiting tube 184 enters the blood flow within lumen 176 downstream of any sharp pressure drops or other flow disturbances associated with the increase in the inner diameter of lumen 176 in the transition region 182. Ribs or wings 188 or another such centering device may be used to hold the distal portion of tube 184 in place.

Figure 11:
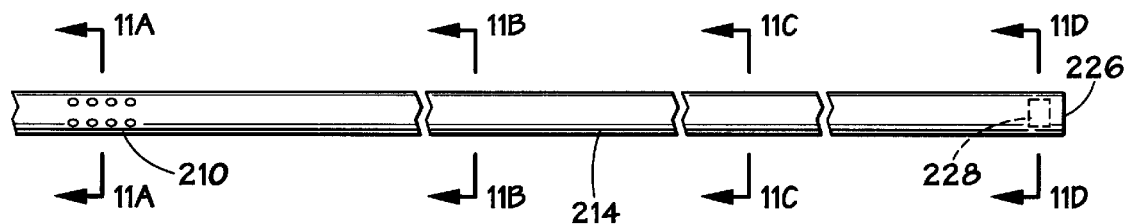
FIG. 11 is a view of part of an alternate exemplary catheter system including an integral blood draw comprising a porous side blood inlet in accordance with the present invention.
Figures 11A, 11B:
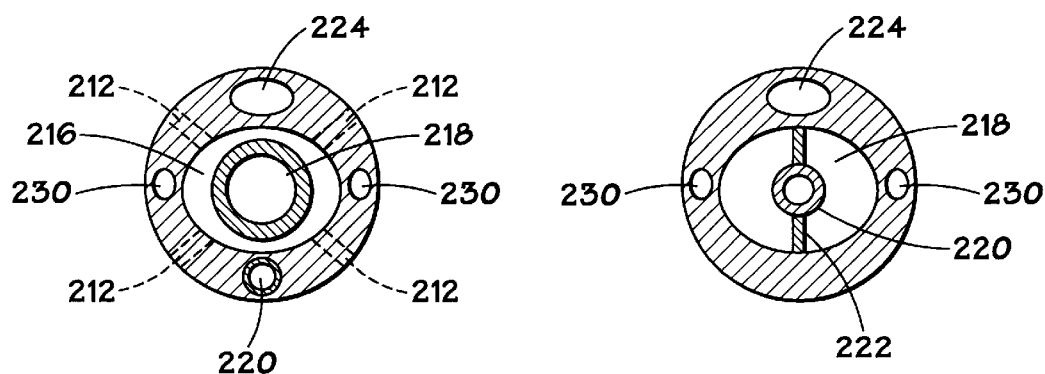
FIG. 11A is a cross-sectional view along line A—A in FIG. 11 of part of an alternate exemplary catheter system including an integral blood draw comprising a porous side blood inlet in accordance with the present invention.
FIG. 11B is a cross-sectional view along line B—B in FIG. 11 of part of an alternate exemplary catheter system including an integral blood draw comprising a porous side blood inlet in accordance with the present invention.
Figures 11C, 11D:
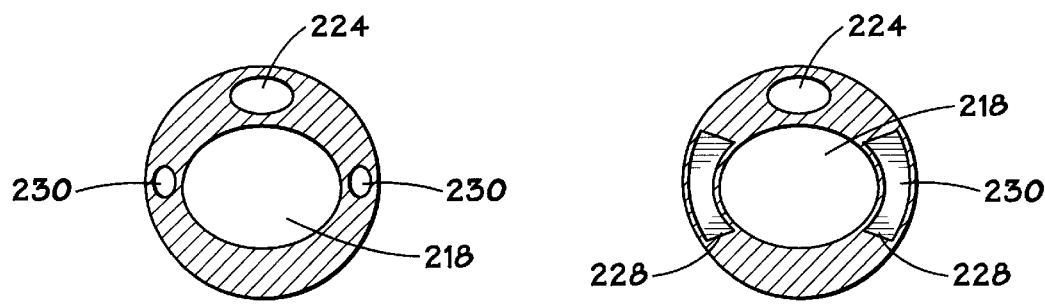
FIG. 11C is a cross-sectional view along line C—C in FIG. 11 of part of an alternate exemplary catheter system including an integral blood draw comprising a porous side blood inlet in accordance with the present invention.
FIG. 11D is a cross-sectional view along line D—D in FIG. 11 of part of an alternate exemplary catheter system including an integral blood draw comprising a porous side blood inlet in accordance with the present invention.

In an alternate embodiment, as shown in FIG. 10, the integral blood inlet of a catheter 190 comprises an axial blood inlet 192. Blood from the patient is drawn from the interior of a guide catheter or sheath, or directly from the patient's vasculature, through the inlet 192, and into catheter outer lumen 194. From there the blood travels through a blood pump (not shown) and is returned to the patient via inner lumen 196. As shown in FIG. 10, the inner lumen 196 includes a proximal portion 198 having relatively smaller internal and external diameters than distal-portion 200, and a transition region 202 joining the two portions. Oxygen-supersaturated fluid supply tube 204, includes a fluid exit port 206 disposed within the distal portion 200 of catheter 190, and ribs or wings 208 may be used to hold the distal portion of tube 204 in place. The proximal portion 198 of inner lumen 196 may be fixed within the interior of outer lumen 194 by a further set or ribs or wings or other similar positioning device. As shown in FIG. 10, the proximal portion 198 of lumen 196 is free to naturally follow a path of least resistance through lumen 194. The proximal portion of tube 204 likewise may be secured within lumen 196 or be free as shown. FIGS. 11 and 11A–D show part of an alternate exemplary catheter system including an integral blood draw. A porous side blood inlet 210 comprising a plurality of channels 212 through the outer wall of catheter 214 allows blood from the patient to enter outer lumen 216. The blood in lumen 216 passes through a blood pump (not shown in FIG. 11) before returning to the patient via lumen 218. Within lumen 218 the blood combines with an oxygen-supersaturated fluid supplied via a tube 220. As shown in FIG. 11, the tube 220, along at least a portion of its length, may be disposed within the lumen 218. The distal tip of the tube 220 is positioned along the longitudinal axis of lumen 218 and secured in place by one or more centering fins or spacers 222.

The catheter 214 also may include a lumen 224 through which blood proximate the distal tip 226 of the catheter 214 may be drawn, e.g. to provide a blood sample for use in determining blood $pO_2$ or in the monitoring of others clinical parameters, to ascertain blood pressure at the distal end of the catheter, etc.

The distal tip 226 of catheter 214 includes an ultrasonic bubble detector 228 or similar assembly for detecting the presence of clinically significant bubbles in the oxygen-enriched fluid delivered to the patient body via lumen 218. Accordingly, the catheter 214 may also include one or more lumens 230 within which leads coupled to the bubble detector 228 are disposed.

FIGS. 12–14 illustrate alternate exemplary tip configurations of a catheter. FIG. 12 shows a straight tip portion 232 including a bubble detector 236 disposed proximate the tip 234 of the catheter. Bubble detector leads 238 comprising one or more pairs of insulated wires or coaxial wires may be disposed as shown for example in FIG. 12A within the catheter side wall. FIG. 13 illustrates a straight tip portion 240 including a dual transducer bubble detector 242, bubble detector leads 244, and a monorail guide lumen 246 through which a guidewire (not shown) may be thread to assist in the placement of the catheter within a patient body. One transducer of a dual transducer bubble detector typically emits an acoustic pulse which is received by the other transducer, and the presence or absence of bubbles is determined by measuring the attenuation of the received signal. FIGS. 14 an 14A illustrate alternate configurations of a catheter tip including a monorail guide lumen 248. The catheter tip as shown in the drawings may include a relatively uniform wall thickness and be of generally circular cross section (FIG. 14), or it may have a varying wall thickness and assume a more tear-drop shape (FIG. 14A).

As shown in FIG. 12, a catheter tip also may include a radiopaque band 250 to aid the physician or caregiver in placing the device. Typically, the band 250 comprises one or more metals or metal alloys, e.g., platinum, gold, tungsten, and iridium, and platinum-iridium and other high density materials that are visible under fluoroscopy.

Figure 15:
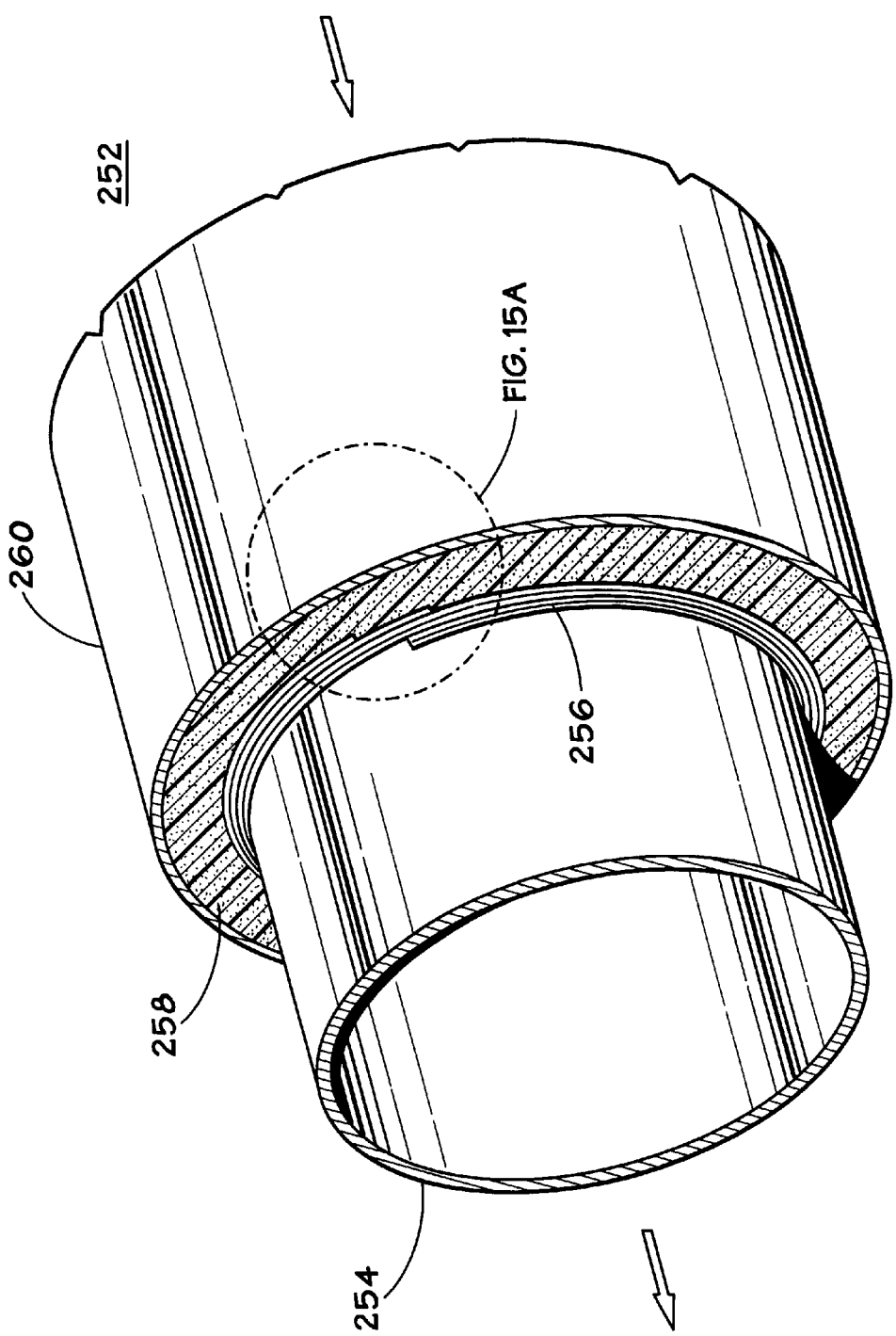
FIG. 15 is an isometric view of an exemplary bubble detector transducer in accordance with the present invention.

A further exemplary bubble detector transducer 252 is shown in FIGS. 15 and 15A. The transducer 252, which may be bonded or otherwise fixedly attached to or within the distal portion of the catheter, may include a single transducer operable in a pulse echo mode, i.e., it can send out an acoustic pulse and sense its reflection. The transducer 252 includes an inner sleeve 254, a layer of wrapped piezoelectric film 256, a metal band 258, and an outer jacket 260. The inner sleeve 254 comprises a polyimide sleeve. The wrapped film 256 comprises a metallized polyvinylidenefluoride (PVDF) film including a conductive upper layer 262, a conductive lower layer 264, and an insulative inner layer 263 separating the upper and lower layers. As shown in the drawings, the metallized film is folded and then wrapped at least once (typically about two to five times) about the inner sleeve 254. This folding permits the use of thinner film that exhibits higher capacitance and lower impedance than a more conventional transducer so that the wire leads 266, which are long, thin wires, maybe driven better. Wire leads 266 are connected to the outermost surfaces of the layers 262, 264 with a conductive epoxy 268. The band 258 may comprise a foil of aluminum or a band of a metal which reflects the outward acoustic pulse. The band 258 comprises a radiopaque material so that the band may also act as a marker to promote placement of the device. The outer jacket 260 may be made of pebax or another suitable material which provides support to the structure. It should further be understood that the bubble detector illustrated in FIGS. 15 and 15A is advantageously a compact device, e.g., air spaces between the layers of the bubble detector are minimized or eliminated. For example, any air voids may be filled with an epoxy or other suitable filler material.

The electronic circuitry 271 associated with the bubble detector transducer 252 causes the transducer 252 to emit ultrasonic pulses typically in the range of 20–30 MHz. In the pulse echo mode, these ultrasonic pulses are transmitted in a pulse train having a frequency of about 20–50 kHz. Thus, approximately ten reflections may be sampled from a single bubble as it passes by the transducer 252, which is about 1 to 1.5 millimeters in length. After the pulses of ultrasonic energy are delivered during a positive portion of this duty cycle, the circuitry 271 waits approximately 0.5 microseconds to allow for a "ring down" period. Then, the reflected signals may be measured, typically for at least three bounces, before the next ultrasonic signals are transmitted.

The present invention has been described in terms of exemplary embodiments. In accordance with the present invention, the operating parameters for the system may be varied, typically with a physician or caregiver specifying and selecting, them for the desired clinical indication. Further, it is contemplated that other embodiments, which may be readily devised by persons of ordinary skill in the art based on the teachings set forth herein, may be within the scope of the invention which is defined by the appended claims. The present invention may be modified and practiced in different but equivalent manners that will be apparent to those skilled in the art having the benefit of the teachings set forth herein.

No limitations are intended to the details or construction or design shown herein, other than as described in the claims appended hereto. Thus, it should be clear that the specific embodiments disclosed above may be altered and modified, and that all such variations and modifications are within the spirit and scope of the present invention as set forth in the claims appended hereto.

What is claimed is:

1. A method for forming a gas-enriched fluid for delivery to a patient, the method comprising the acts of:
   providing a first fluid passageway adapted to transmit a first fluid;
   providing a second fluid passageway adapted to transmit a gas-supersaturated fluid;
   providing an intersection of the first fluid passageway with the second fluid passageway, the intersection being adapted to form a gas-enriched fluid from a combination of the first fluid and the gas-supersaturated fluid; and
   providing a third fluid passageway having a lumen adapted to deliver the gas-enriched fluid to the patient, wherein at least a distal portion of the second fluid passageway is disposed within the lumen of the third fluid passageway.

2. The method of claim 1 wherein the first fluid comprises blood.

3. The method of claim 1 wherein the gas-supersaturated fluid comprises an oxygen-supersaturated fluid.

4. The method of claim 1 wherein the first fluid comprises a blood substitute.

5. The method of claim 1 wherein the gas-enriched fluid comprises an oxygen-enriched physiologic liquid.

6. The method of claim 1 comprising the act of:
   providing a pump adapted to transfer the first fluid through the first fluid passageway.

7. The method of claim 1 comprising the act of:
   providing a supply of the first fluid.

8. The method of claim 1 wherein the first fluid passageway is adapted to couple to a supply of the first fluid.

9. The method of claim 1 comprising the act of:
   providing a supply of the gas-supersaturated fluid.

10. The method of claim 1 wherein the second fluid passageway is adapted to couple to a supply of the gas-supersaturated fluid.

11. The method of claim 1, wherein the distal portion of the second fluid passageway is secured within the lumen of the third fluid passageway by at least one spacer.

12. The method of claim 1, wherein the distal portion of the second fluid passageway comprises an array of capillaries.

* * * * *